US012357835B2

(12) United States Patent
Maharbiz et al.

(10) Patent No.: US 12,357,835 B2
(45) Date of Patent: Jul. 15, 2025

(54) ULTRASOUND-BASED PROTOCOL FOR OPERATING AN IMPLANTABLE DEVICE

(71) Applicant: Iota Biosciences, Inc., Alameda, CA (US)

(72) Inventors: Michel M. Maharbiz, El Cerrito, CA (US); Joshua Kay, Oakland, CA (US); Jose M. Carmena, Alameda, CA (US)

(73) Assignee: IOTA BIOSCIENCES, INC., Alameda, CA (US)

( * ) Notice: Subject to any disclaimer, the term of this patent is extended or adjusted under 35 U.S.C. 154(b) by 800 days.

(21) Appl. No.: 17/420,355

(22) PCT Filed: Jan. 3, 2020

(86) PCT No.: PCT/US2020/012246
§ 371 (c)(1),
(2) Date: Jul. 1, 2021

(87) PCT Pub. No.: WO2020/142732
PCT Pub. Date: Jul. 9, 2020

(65) Prior Publication Data
US 2022/0143414 A1      May 12, 2022

Related U.S. Application Data

(60) Provisional application No. 62/788,390, filed on Jan. 4, 2019.

(51) Int. Cl.
*A61N 1/372* (2006.01)
*A61B 5/24* (2021.01)
(Continued)

(52) U.S. Cl.
CPC ............ *A61N 1/37217* (2013.01); *A61B 5/24* (2021.01); *A61N 1/0551* (2013.01); *A61N 1/36135* (2013.01); *A61N 1/3787* (2013.01)

(58) Field of Classification Search
None
See application file for complete search history.

(56) References Cited

U.S. PATENT DOCUMENTS 5,107,833 A *  4/1992  Barsness ............ A61N 1/37223
                                              128/903
5,331,966 A *  7/1994  Bennett .............. A61N 1/36185
                                              128/903
(Continued)

FOREIGN PATENT DOCUMENTS

CN    101612451 A    12/2009
CN    102427849 A     4/2012
(Continued)

OTHER PUBLICATIONS

Arbabian, A. et al. (Dec. 1, 2016, e-pub. Nov. 11, 2016). "Sound Technologies, Sound Bodies: Medical Implants With Ultrasonic Links," IEEE Microwave Magazine 17(12):39-54.
(Continued)

*Primary Examiner* — Curtis J King
(74) *Attorney, Agent, or Firm* — MORRISON & FOERSTER LLP

(57) ABSTRACT

Method and system embodiments for operating a device implantable in a subject using ultrasonic waves are described. In some embodiments, a method is performed at the implantable device to receive ultrasonic waves including an operating mode command. Then, the implantable device sets an operating mode of the implantable device to one operating mode from a plurality of predetermined operating modes based on the operating mode command.

32 Claims, 11 Drawing Sheets

(51) Int. Cl.
  *A61N 1/05*    (2006.01)
  *A61N 1/36*    (2006.01)
  *A61N 1/378*   (2006.01)

(56) References Cited

U.S. PATENT DOCUMENTS

| | | | |
|---|---|---|---|
| 5,693,076 A * | 12/1997 | Kaemmerer | A61N 1/37247 |
| | | | 607/30 |
| 6,170,488 B1 | 1/2001 | Spillman, Jr. | |
| 6,185,452 B1 | 2/2001 | Schulman et al. | |
| 6,480,743 B1 * | 11/2002 | Kirkpatrick | A61N 1/36135 |
| | | | 607/45 |
| 7,069,086 B2 | 6/2006 | Von Arx | |
| RE42,934 E | 11/2011 | Thompson | |
| 8,214,164 B2 | 7/2012 | Gandhi et al. | |
| 8,301,262 B2 | 10/2012 | Mi et al. | |
| 8,786,134 B2 | 7/2014 | Kazama | |
| 9,544,068 B2 | 1/2017 | Arbabian | |
| 9,731,141 B2 | 8/2017 | Tran | |
| 10,014,570 B2 | 7/2018 | Arbabian | |
| 10,118,054 B2 | 11/2018 | Maharbiz | |
| 10,177,606 B2 | 1/2019 | Charthad | |
| 10,300,309 B2 | 5/2019 | Maharbiz | |
| 10,300,310 B2 | 5/2019 | Maharbiz | |
| 10,576,305 B2 | 3/2020 | Maharbiz | |
| 10,682,530 B2 | 6/2020 | Maharbiz | |
| 10,744,347 B2 | 8/2020 | Maharbiz | |
| 10,765,865 B2 | 9/2020 | Maharbiz | |
| 10,898,736 B2 | 1/2021 | Maharbiz et al. | |
| 11,033,746 B2 | 6/2021 | Maharbiz et al. | |
| 11,246,990 B2 * | 2/2022 | Brauker | A61M 5/31525 |
| 11,589,748 B2 | 2/2023 | Maharbiz | |
| 11,601,019 B2 | 3/2023 | Arbabian | |
| 11,607,128 B2 | 3/2023 | Maharbiz | |
| 11,717,689 B2 | 8/2023 | Maharbiz et al. | |
| 11,786,124 B2 | 10/2023 | Maharbiz et al. | |
| 11,890,474 B2 | 2/2024 | Carmena | |
| 11,969,596 B2 | 4/2024 | Carmena | |
| 12,004,840 B2 | 6/2024 | Maharbiz | |
| 2002/0013612 A1 * | 1/2002 | Whitehurst | A61N 1/36096 |
| | | | 607/45 |
| 2002/0156504 A1 * | 10/2002 | Chen | A61N 1/3956 |
| | | | 607/5 |
| 2003/0060163 A1 * | 3/2003 | Filkins | G01S 15/10 |
| | | | 455/67.14 |
| 2003/0229383 A1 * | 12/2003 | Whitehurst | A61N 1/372 |
| | | | 607/60 |
| 2004/0030260 A1 | 2/2004 | Arx | |
| 2004/0106967 A1 * | 6/2004 | Von Arx | A61N 1/37229 |
| | | | 607/60 |
| 2004/0147969 A1 * | 7/2004 | Mann | A61B 5/02108 |
| | | | 607/17 |
| 2006/0122663 A1 * | 6/2006 | Mandell | A61N 1/3601 |
| | | | 607/48 |
| 2006/0136004 A1 * | 6/2006 | Cowan | A61N 1/3621 |
| | | | 607/33 |
| 2006/0149324 A1 * | 7/2006 | Mann | A61N 1/37254 |
| | | | 607/9 |
| 2006/0265022 A1 * | 11/2006 | John | A61N 2/006 |
| | | | 607/45 |
| 2007/0078490 A1 * | 4/2007 | Cowan | A61N 1/3756 |
| | | | 607/9 |
| 2007/0150019 A1 | 6/2007 | Youker | |
| 2008/0228090 A1 * | 9/2008 | Wariar | A61B 5/145 |
| | | | 600/300 |
| 2009/0024054 A1 * | 1/2009 | Lazarus | A61B 5/6846 |
| | | | 600/549 |
| 2009/0124875 A1 * | 5/2009 | Bentsen | A61B 5/1455 |
| | | | 600/341 |
| 2009/0138058 A1 * | 5/2009 | Cooke | A61N 1/3718 |
| | | | 607/30 |
| 2009/0157144 A1 * | 6/2009 | Kelly | A61N 1/37276 |
| | | | 607/60 |
| 2009/0198307 A1 | 8/2009 | Mi et al. | |
| 2009/0222065 A1 * | 9/2009 | Dlugos, Jr. | A61B 5/03 |
| | | | 607/60 |
| 2010/0131033 A1 * | 5/2010 | Cantatore | H01Q 1/2225 |
| | | | 607/60 |
| 2012/0169336 A1 * | 7/2012 | Leigh | A61B 5/7203 |
| | | | 324/309 |
| 2013/0027186 A1 * | 1/2013 | Cinbis | A61B 5/0028 |
| | | | 340/10.1 |
| 2013/0046354 A1 * | 2/2013 | Frustaci | A61N 1/3987 |
| | | | 607/6 |
| 2013/0172774 A1 * | 7/2013 | Crowder | G16H 40/63 |
| | | | 600/300 |
| 2013/0218251 A1 | 8/2013 | Penner | |
| 2014/0200638 A1 * | 7/2014 | Chow | A61N 1/36125 |
| | | | 607/116 |
| 2014/0336474 A1 | 11/2014 | Arbabian | |
| 2015/0012057 A1 * | 1/2015 | Carlson | A61N 1/3606 |
| | | | 607/45 |
| 2016/0015986 A1 * | 1/2016 | Seeberger | A61N 1/371 |
| | | | 607/28 |
| 2016/0156229 A1 | 6/2016 | Sakata | |
| 2016/0250486 A1 * | 9/2016 | Yoder | G16Z 99/00 |
| | | | 340/870.07 |
| 2017/0064462 A1 * | 3/2017 | Warren | A61N 1/36038 |
| 2017/0117753 A1 | 4/2017 | Charthad | |
| 2017/0125892 A1 * | 5/2017 | Arbabian | A61B 5/0024 |
| 2017/0135633 A1 * | 5/2017 | Connor | A61N 1/36557 |
| 2017/0201130 A1 | 7/2017 | Park | |
| 2017/0312530 A1 * | 11/2017 | Schilling | A61B 5/0031 |
| 2017/0319858 A1 | 11/2017 | Radziemski et al. | |
| 2018/0000344 A1 * | 1/2018 | Melodia | A61B 5/0026 |
| 2018/0027077 A1 * | 1/2018 | Melodia | G16H 40/67 |
| | | | 370/254 |
| 2018/0085605 A1 | 3/2018 | Maharbiz | |
| 2019/0022427 A1 | 1/2019 | Maharbiz | |
| 2019/0022428 A1 | 1/2019 | Maharbiz | |
| 2019/0150881 A1 | 5/2019 | Maharbiz | |
| 2019/0150882 A1 | 5/2019 | Maharbiz | |
| 2019/0150883 A1 | 5/2019 | Maharbiz | |
| 2019/0150884 A1 | 5/2019 | Maharbiz | |
| 2019/0321640 A1 | 10/2019 | Carmena | |
| 2019/0321644 A1 | 10/2019 | Maharbiz | |
| 2019/0358460 A1 | 11/2019 | Alford | |
| 2020/0023208 A1 | 1/2020 | Maharbiz | |
| 2020/0023209 A1 | 1/2020 | Maharbiz | |
| 2020/0105151 A1 * | 4/2020 | Mahkonen | H04W 4/46 |
| 2020/0114175 A1 | 4/2020 | Maharbiz | |
| 2020/0230441 A1 | 7/2020 | Maharbiz | |
| 2020/0252730 A1 * | 8/2020 | Frieding | A61B 5/121 |
| 2020/0257136 A1 | 8/2020 | Arbabian et al. | |
| 2020/0289857 A1 | 9/2020 | Maharbiz | |
| 2020/0324148 A1 | 10/2020 | Maharbiz | |
| 2020/0327975 A1 * | 10/2020 | Barthelaix | G16H 20/40 |
| 2021/0037544 A1 * | 2/2021 | Andrews | H04W 72/121 |
| 2021/0146144 A1 * | 5/2021 | Jimenez | A61B 5/0022 |
| 2021/0268294 A1 | 9/2021 | Maharbiz et al. | |
| 2021/0308462 A1 * | 10/2021 | Carmena | A61N 1/36132 |
| 2021/0392720 A1 * | 12/2021 | Fang | H04W 72/1221 |
| 2022/0047869 A1 | 2/2022 | Carmena et al. | |
| 2022/0062650 A1 | 3/2022 | Maharbiz et al. | |
| 2022/0387791 A1 * | 12/2022 | Bakker | A61N 1/0531 |
| 2023/0089015 A1 | 3/2023 | Maharbiz et al. | |
| 2023/0095948 A1 | 3/2023 | Maharbiz et al. | |
| 2023/0233851 A1 | 7/2023 | Neely et al. | |
| 2023/0301514 A1 | 9/2023 | Lepe et al. | |
| 2023/0414950 A1 | 12/2023 | Maharbiz | |
| 2024/0017071 A1 | 1/2024 | Carmena | |
| 2024/0024032 A1 | 1/2024 | Kay | |
| 2024/0099584 A1 | 3/2024 | Maharbiz | |
| 2024/0100327 A1 | 3/2024 | Carmena | |
| 2024/0108882 A1 | 4/2024 | Maharbiz | |

FOREIGN PATENT DOCUMENTS

| | | | |
|---|---|---|---|
| CN | 103079633 A | 5/2013 | |
| CN | 108136439 A | 6/2018 | |
| CN | 108430570 A | 8/2018 | |
| CN | 108604824 A | 9/2018 | |

(56) References Cited

FOREIGN PATENT DOCUMENTS

| | | |
|---|---|---|
| JP | 2005535391 A | 11/2005 |
| JP | 2007313336 A | 12/2007 |
| JP | 2010239781 A | 10/2010 |
| JP | 2011508871 A | 3/2011 |
| JP | 2016512677 A | 4/2016 |
| JP | 2019524224 A | 9/2019 |
| JP | 2019524230 A | 9/2019 |
| JP | 2019527568 A | 10/2019 |
| JP | 2020500048 A | 1/2020 |
| KR | 20140082628 A | 7/2014 |
| WO | 200232502 A1 | 4/2002 |
| WO | 2010131157 A1 | 11/2010 |
| WO | 2011112773 A2 | 9/2011 |
| WO | 2014121296 A1 | 8/2014 |
| WO | 2014174790 A1 | 10/2014 |
| WO | 2015142842 A2 | 9/2015 |
| WO | 2015142842 A3 | 11/2015 |
| WO | 2017015506 A1 | 1/2017 |
| WO | 2017116752 A1 | 7/2017 |
| WO | 2017120560 A1 | 7/2017 |
| WO | 2018009905 A2 | 1/2018 |
| WO | 2018009908 A1 | 1/2018 |
| WO | 2018009910 A1 | 1/2018 |
| WO | 2018009911 A1 | 1/2018 |
| WO | 2018009912 A1 | 1/2018 |
| WO | 2018009905 A3 | 2/2018 |
| WO | 2018081793 A1 | 5/2018 |
| WO | 2019075203 A1 | 4/2019 |
| WO | 2019204769 A1 | 10/2019 |
| WO | 2019204773 A1 | 10/2019 |
| WO | 2020047152 A1 | 3/2020 |
| WO | 2020117967 A1 | 6/2020 |
| WO | 2020142732 A1 | 7/2020 |
| WO | 2020142733 A1 | 7/2020 |
| WO | 2021077020 A1 | 4/2021 |
| WO | 2021077022 A1 | 4/2021 |
| WO | 2021168163 A1 | 8/2021 |
| WO | 2021168229 A1 | 8/2021 |
| WO | 2021248013 A1 | 12/2021 |
| WO | 2022035889 A1 | 2/2022 |
| WO | 2022046770 A1 | 3/2022 |
| WO | 2023183891 A2 | 9/2023 |
| WO | 2024011141 A2 | 1/2024 |
| WO | 2024086662 A1 | 4/2024 |
| WO | 2024167868 A2 | 8/2024 |
| WO | 2024182632 A2 | 9/2024 |
| WO | 2024263722 A1 | 12/2024 |
| WO | 2024263730 A1 | 12/2024 |
| WO | 2024263796 A2 | 12/2024 |

OTHER PUBLICATIONS

Bertrand, A. et al. (Aug. 2014). "Beamforming Approaches for Untethered, Ultrasonic Neural Dust Motes for Cortical Recording: A Simulation Study," IEEE EMBC, 2625-2628.

Grossman, N. et al. (Jun. 1, 2017). "Noninvasive Deep Brain Stimulation via Temporally Interfering Electric Fields," Cell 169:1029-1041.

International Preliminary Report on Patentability, issued Jun. 16, 2021 for PCT Application No. PCT/US2020/012246, filed Jan. 3, 2020, 8 pages.

International Search Report and Written Opinion, mailed Mar. 10, 2020, for PCT Application No. PCT/US2020/012246, filed Jan. 3, 2020, 12 pages.

Seo, D. et al. (Jul. 8, 2013). "Neural Dust: Ultrasonic Low Power Solution for Chronic Brain-Machine Interfaces," Dept. of Electrical Engineering and Computer Sciences Berkley, CA. pp. 1-11.

Shmilovitz et al. (Apr. 2014). "Noninvasive Control of the Power Transferred to an Implanted Device by an Ultrasonic Transcutaneous Energy Transfer Link," IEEE Transaction on Bio medical Engineering 61(4):1-10.

Taylor, J. et al. (2004). "Multiple-Electrode Nerve Cuffs for Low-Velocity and Velocity-Selective Neural Recording," Medical & Biological Engineering & Computing 42:634-643.

U.S. Appl. No. 18/099,882, Maharbiz et al., filed Jan. 20, 2023.
U.S. Appl. No. 18/111,499, Maharbiz et al., filed Feb. 17, 2023.
U.S. Appl. No. 18/414,173, Carmena et al., filed Jan. 16, 2024.
U.S. Appl. No. 18/447,228, Maharbiz et al., filed Aug. 9, 2023.

Wodlinger, B. et al. (Oct. 2009). "Localization and Recovery of Peripheral Neural Sources With Beamforming Algorithms," IEEE Transactions on Neural Systems and Rehabilitation Engineering 17(5):461-468, 18 pages.

Bin, Y. (2006). "7.3 The Operating Modes and Programming of 8253," in Microcomputer Principles and Interface Technology, Southwest Jiaotong University Press, Chengdu, China, 24 pages. (English Translation).

Ji, Y. (2011). "6.5.7 Fieldbus Drive," in CNC System Software Design Based on Industrial Control Programming Language IEC6113-3, Beijing University of Aeronautics and Astronautics Press, Beijing, China, 16 pages. (English Translation).

U.S. Appl. No. 19/026,030, Maharbiz et al., filed Jan. 16, 2025.

\* cited by examiner

ULTRASOUND-BASED PROTOCOL FOR OPERATING AN IMPLANTABLE DEVICE

CROSS-REFERENCE TO RELATED APPLICATION

This application is a U.S. national phase application under 35 U.S.C. § 371 of International Application No. PCT/US2020/012246, filed on Jan. 3, 2020, which claims priority benefit to U.S. Provisional Application No. 62/788,390, filed on Jan. 4, 2019, the entire disclosure of each of which is incorporated herein by reference for all purposes.

FIELD OF THE DISCLOSURE

The present disclosure relates generally to operating an implantable device and, more specifically, to operating the implantable device using ultrasonic waves.

BACKGROUND OF THE DISCLOSURE

Invasive methods have been developed for treating various medical conditions of a patient. These methods may involve inserting an implantable medical device (IMD) such as a cardiac or neural bio-implant within the patient's body. Operating such implantable devices in a wireless fashion remains a technical challenge for many biomedical applications. This is, in part, because the traditional approach of using radio frequencies (RF) to control wireless devices has many limitations in the biomedical context and may pose a health hazard to the patient. For example, RF antenna needed to process RF may have a large form factor and would render the implantable device using the RF antenna too large to be safely and comfortably placed at many locations in the body.

Moreover, biological tissue tends to easily absorb energy from RF carrier frequencies, which may limit the implantable depth of the implantable device. In addition, due to the high absorption rate of RF energy, biological tissue may more likely overheat and pose a health hazard to the patient.

The disclosures of all publications, patents, and patent applications referred to herein are each hereby incorporated by reference in their entireties. To the extent that any reference incorporated by reference conflicts with the instant disclosure, the instant disclosure shall control.

SUMMARY OF THE DISCLOSURE

As discussed above, there is a need for implantable devices having a smaller form factor (e.g., in mm and sub-mm dimensions) to increase biocompatibility and reduce the invasiveness and discomfort caused by larger implantable devices controlled using, for example, RF. In some embodiments, to achieve this smaller form factor, an implantable device can be configured to be operated and powered using ultrasonic waves receivable at one or more ultrasonic transducers of the implantable device.

In some embodiments, using ultrasonic waves to operate and power the implantable device can be advantageous over other approaches because biological tissues have significantly lower absorption rates of ultrasonic waves than other types of waves such as RF waves. This property of ultrasonic waves can allow the device to be implantable at greater depths in the subject as well as to reduce tissue heating due to energy absorbed by the tissue.

In some embodiments, to address the needs noted above, a device implantable in a subject includes: an ultrasonic transducer configured to receive ultrasonic waves including an operating mode command; and a controller circuit configured to set an operating mode of the implantable device to one operating mode from a plurality of operating modes based on the operating mode command.

In some embodiments, the plurality of operating modes includes one or more of a downlink mode for downloading data from the received ultrasonic waves, or an uplink mode for uploading data generated at the implantable device to an external device using the received ultrasonic waves. In some embodiments, the plurality of operating modes includes the downlink mode and the uplink mode.

In some embodiments, the ultrasonic waves are received from an interrogator.

In some embodiments, the ultrasonic waves are received from another implantable device.

In some embodiments, the method includes: determining that the operating mode command corresponds to a pattern from a plurality of predetermined patterns; and setting the operating mode based on the determined pattern.

In some embodiments, determining that the operating mode command corresponds to the pattern includes: determining that a first portion of the operating mode command corresponds to the determined pattern.

In some embodiments, the first portion includes a single pulse that indicates a start of the operating mode command. In some embodiments, the first portion includes a sequence of two or more pulses.

In some embodiments, the plurality of predetermined patterns includes a plurality of corresponding pulse durations, a plurality of corresponding amplitudes, or a plurality of corresponding phase or frequency changes.

In some embodiments, the plurality of predetermined patterns includes a plurality of corresponding pulse durations, and one or more of the pulse durations are set based on a carrier signal period of the received ultrasonic waves.

In some embodiments, determining that the operating mode command corresponds to the pattern includes: converting the ultrasonic waves into an electrical signal including a representation of the operating mode command; and counting a number of instances that a first portion of the electrical signal crosses a predefined voltage level, and the number of instances corresponds to the determined pattern.

In some embodiments, the determined pattern is associated with uploading data, and the operating mode command includes a second portion different from the first portion, and the method includes: setting the operating mode to an uplink mode for uploading device data associated with the uplink mode; and backscattering the ultrasonic waves, the backscattered ultrasonic waves encoding the device data in a backscatter of the second portion of the operating mode command.

In some embodiments, the uplink mode includes an acknowledgement mode and the device data includes an acknowledgement that the implantable device successfully extracted an operating instruction from second ultrasonic waves received by the implantable device.

In some embodiments, the uplink mode includes a physiological-condition reporting mode, and the device data includes information associated with a physiological condition detected by the implantable device in the physiological-condition reporting mode.

In some embodiments, the uplink mode includes a neural-activity reporting mode, and the device data includes information associated with an electrophysiological signal detected by the implantable device in the neural-activity reporting mode.

In some embodiments, the device data includes information associated with an electrical pulse emitted by the implantable device, and the electrical pulse is configured to modulate activity of a target nerve.

In some embodiments, the implantable device is configured to emit the electrical pulse in response to an operating instruction extracted from second ultrasonic waves received by the implantable device when the operating mode of the implantable device was set to a downlink mode.

In some embodiments, the determined pattern is associated with downloading data, the operating mode command includes a second portion different from the first portion, and the method includes: setting the operating mode to a downlink mode for extracting data from the second portion of the operating mode command.

In some embodiments, the extracted data is associated with measuring a physiological condition, and the method includes: in response to extracting the data, measuring the physiological condition.

In some embodiments, the physiological condition includes a temperature, a pulse rate, a blood pressure, a pH level, a presence of an analyte, or a concentration of the analyte. In some embodiments, the physiological condition includes a concentration of an analyte, and the analyte is oxygen or glucose.

In some embodiments, the extracted data is associated with recording an electrophysiological signal, and the implantable device includes two or more electrodes that are in electrical communication with a nerve of a subject, and the two or more electrodes are configured to record the electrophysiological signal. In some embodiments, the method includes recording the electrophysiological signal in response to the data extracted from the second portion.

In some embodiments, the extracted data is associated with stimulating a nerve, the implantable device includes two or more electrodes that are in electrical communication with the nerve of a subject, and the method includes: emitting one or more electrical pulses configured to modulate activity of the nerve using the two or more electrodes in response to the data extracted from the second portion.

In some embodiments, the method includes: maintaining a current operating state of the implantable device based on operation logic that define transitions between operating states, wherein the implantable device is configured to operate according to the current operating state; transitioning from the current operating state to a next operating state of the operation logic based on the operating mode command; and configuring the implantable device to operate according to the next operating state.

In some embodiments, the operation logic is implemented by a microprocessor or a microcontroller of the implantable device. In some embodiments, the operation logic is implemented by a finite state machine (FSM).

In some embodiments, an implantable device operated using ultrasonic waves includes: an ultrasonic transducer configured to receive ultrasonic waves including an operating mode command; and a controller circuit configured to set an operating mode of the implantable device to one operating mode from a plurality of operating modes based on the operating mode command.

Further described herein are various system embodiments for operating an implantable device using ultrasonic waves, according to any of the aforementioned method embodiments.

BRIEF DESCRIPTION OF THE DRAWINGS

The foregoing summary, as well as the following detailed description of embodiments, is better understood when read in conjunction with the appended drawings. For the purpose of illustrating the present disclosure, the drawings show example embodiments of the disclosure; the disclosure, however, is not limited to the specific methods and instrumentalities disclosed. In the drawings.

DETAILED DESCRIPTION

Described herein are systems and methods for operating a device implantable within a subject using ultrasonic waves. As discussed above, the use of ultrasonic waves may enable the implantable device to retain a small form factor and greater implantable depths and to be operated safely. In some embodiments, to enable such an implantable device to be wirelessly operated, the implantable device can be configured to include an ultrasonic transducer configured to receive ultrasonic waves including an operating mode command. The implantable device can also include a controller circuit configured to set an operating mode of the implantable device to one operating mode from a plurality of stored operating modes based on the operating mode command.

In some embodiments, the implantable device can be configured to determine whether the operating mode command corresponds to a pattern from a plurality of predetermined patterns based on a first portion of the operating mode command. Then, the implantable device can set an operating state corresponding to the operating mode based on the determined pattern. In some embodiments, the implantable device can be configured to operate in an uplink mode from a plurality of operating modes or to operate in a downlink mode from a plurality of operating modes depending on the determined pattern.

In some embodiments, in the uplink mode, the implantable device can be configured to encode device information in a backscatter of a second portion of the operating mode command. Example uplink modes may include a mode for uploading sensor data (e.g., device information) such as a neural activity, a detected temperature, a pH level, a concentration of an analyte, etc. Another example uplink mode may include a mode to transmit an acknowledgement (e.g., device information) of previously-received data. Another example uplink mode may include a mode for transmitting power information (e.g., device information) generated at the implantable device.

In some embodiments, in the downlink mode, the implantable device can be configured to decode data from a second portion of the operating mode command. Example downlink modes may include a mode for downloading device parameters from the received ultrasonic waves. Another example downlink mode may be a mode for selecting a next operating mode based on the decoded data.

Figure 1:
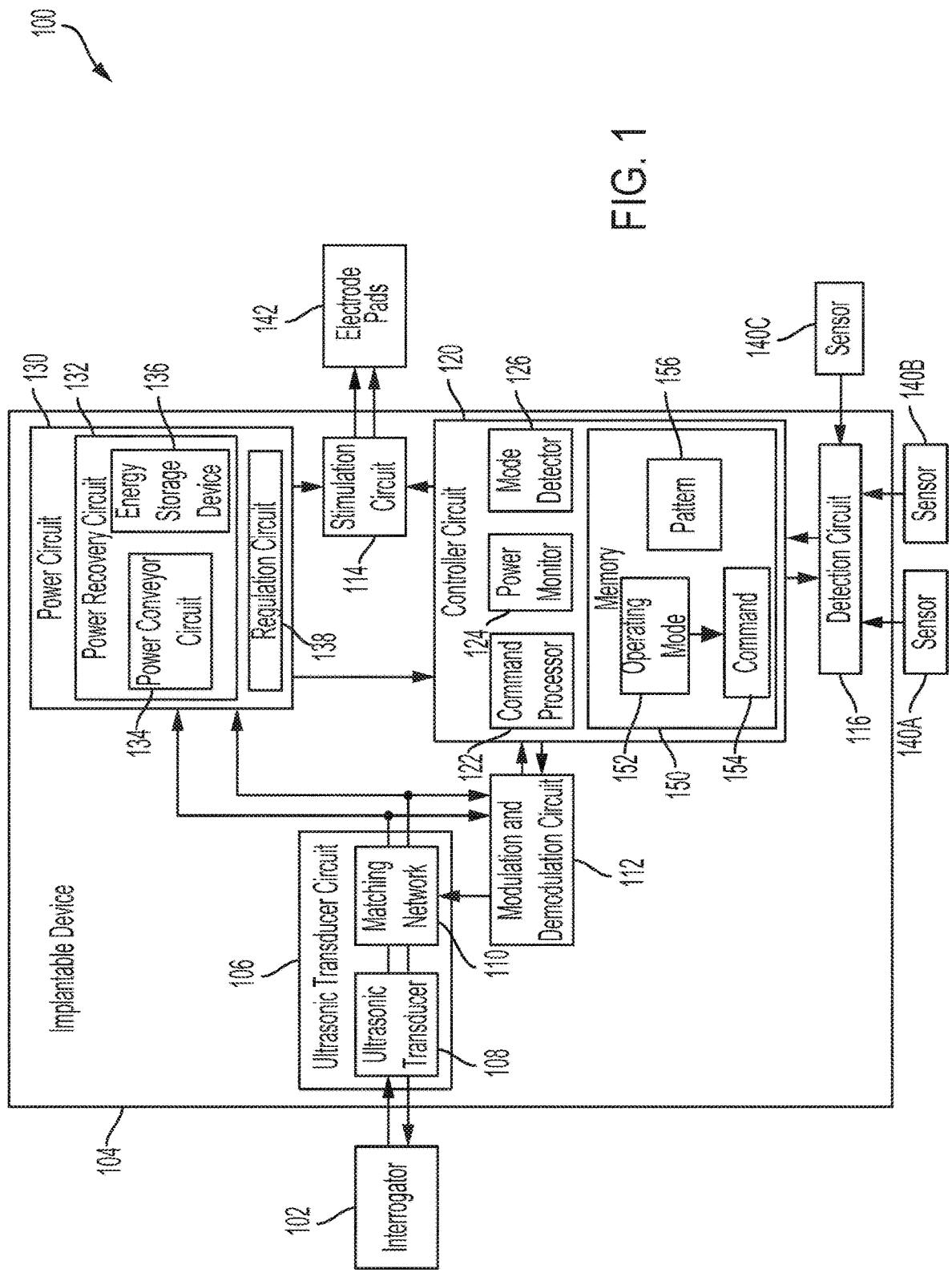
FIG. 1 illustrates a system for operating an implantable device using ultrasonic waves, according to some embodiments.

FIG. 1 illustrates a system 100 for operating an implantable device 104 using ultrasonic waves, according to some embodiments. In some embodiments, implantable device 104 can be wirelessly powered and operating by ultrasonic waves transmitted from interrogator 102, as will be further described below with respect to FIG. 2. In some embodiments, implantable device 104 can be configured to wirelessly communicate with interrogator 102 through ultrasonic communication. In some embodiments, implantable device 104 can be configured to wirelessly communicate with one or more other implantable devices through ultrasonic communication. In some embodiments, implantable device 104 can be implanted within a subject such as a patient and interrogator 102 can be a separate device that is external to (i.e., non-implanted) or fully-implanted in the subject.

In some embodiments, to enable implantable device 104 to be operated using ultrasonic waves, implantable device 104 can include the following device components: an ultrasonic transducer circuit 106, a modulation and demodulation circuit 112, a stimulation circuit 114, a detection circuit 116, a controller circuit 120, and a power circuit 130. In some embodiments, one or more of these device components can be implemented as a digital circuit, an analog circuit, or a mixed-signal integrated circuit depending on their operations. For example, controller circuit 120 may include a microprocessor, a finite state machine (FSM), a field programmable gate array (FPGA), or a microcontroller.

In some embodiments, ultrasonic transducer circuit 106 includes an ultrasonic transducer 108 coupled to a matching network 110. In some embodiments, ultrasonic transducer circuit 106 does not include matching network 110. In some embodiments, ultrasonic transducer 108 can be configured to receive ultrasonic waves from interrogator 102 and convert energy from the received ultrasonic waves into an electrical signal to power one or more device components of implantable device 104. In some embodiments, the electrical signal can be generated by ultrasonic transducer 108 because vibrations of ultrasonic transducer 108 caused by the received ultrasonic waves induce a voltage across the electric terminals of ultrasonic transducer 108, which causes an electrical current to flow.

In some embodiments, as described above, power from the received ultrasonic waves can be used by implantable device 104 to power its device components; accordingly, these ultrasonic waves are sometimes referred to herein as powering ultrasonic waves. In some embodiments, the received ultrasonic waves can encode information including operating mode commands for operating the implantable device; accordingly, these ultrasonic waves are sometimes referred to herein as communication ultrasonic waves. In some embodiments, similar to how powering ultrasonic waves can be processed, the communication ultrasonic waves can be received by ultrasonic transducer 108 to generate an electrical signal having an electrical current that flows through ultrasonic transducer 108. In some embodiments, the generated electrical signal encodes the operating mode commands in the electrical current. In some embodiments, the same ultrasonic waves can be configured to both power implantable device 104 and to encode information for transmitting to implantable device 104. In some embodiments, as will be further described below with respect to FIG. 3, each operating mode command can include one or more ultrasound pulses and each ultrasound pulse may include one or more carrier cycles of ultrasonic waves.

In some embodiments, ultrasonic transducer circuit 106 includes a plurality of ultrasonic transducers coupled to a plurality of corresponding matching networks. By including at least two ultrasonic transducers, implantable device 104 can be configured to be powered by electrical signals generated by the at least two ultrasonic transducers to more efficiently and consistently extract power provided by interrogator 102, according to some embodiments. In some embodiments, implantable device 104 can be configured to harvest power from one or more ultrasonic transducers selected from the plurality of ultrasonic transducers. For example, implantable device 104 may select an ultrasonic transducer that provides the highest power or the most consistent power.

For example, a host of factors such as an orientation of ultrasonic transducer or intervening biological material between ultrasonic transducer 108 and an ultrasonic wave source interrogator 102 may significantly reduce the power receivable at ultrasonic transducer 108. By adding one or more additional ultrasonic transducers, reduced power receivable at a single ultrasonic transducer (e.g., ultrasonic transducer 108) may be less likely to negatively impact operations of implantable device 104.

In some embodiments, including at least two ultrasonic transducers may enable implantable device 102 to be more reliably controlled using ultrasonic waves. For example, implantable device 102 may be configured to compare the signal strength of the at least two ultrasonic transducers and select the signal having a highest signal strength to operate implantable device 102. In some embodiments, implantable device 102 can use a selected ultrasonic transducer to receive communication from (i.e., during downlink) and to backscatter information on (i.e., during uplink). In some embodiments, implantable device 102 can select a first ultrasonic transducer from the at least two ultrasonic transducers to receive ultrasonic communications for downlink ultrasonic communication and select a second ultrasonic transducer from the at least two ultrasonic transducers to backscatter encode information for uplink ultrasonic communications. In some embodiments, implantable device 102 can be configured to perform beamforming with the at least two ultrasonic transducers to improve the signal to noise ratio of the uplink and downlink ultrasonic communications. In some embodiments, one or more of these ultrasonic transducers can be a micro machined ultrasonic transducer, such as a capacitive micro-machined ultrasonic transducer (CMUT) or a piezoelectric micro-machined ultrasonic transducer (PMUT), or can be a bulk piezoelectric transducer. Additionally implementations of ultrasonic transducer 108 are described below with respect to FIG. 8.

In some embodiments, matching network 110 can be an electronic circuit configured to select an impedance match between the electrical impedance of ultrasonic transducer 108 and the electrical impedance of implantable device 104 (e.g., power circuit 130) to reduce signal reflection. In some embodiments, matching network 110 can be implemented in various configurations of one or more circuit elements such inductors, capacitors, resistors, diodes, transistors, or any combination thereof. For example, matching network 110 may be implemented as a plurality of capacitors connected in parallel and coupled to a plurality of corresponding switches. By controlling which of the switches open or close, matching network 110 may control how the plurality of capacitors is charged to select the impedance. In some embodiments, matching network 110 can be configured to enable the electrical signal generated by ultrasonic transducer 108 to bypass the plurality of capacitors via a separate wire controlled by a switch.

In some embodiments, to enable implantable device 104 to be powered using ultrasonic waves, power circuit 130 can include a power recovery circuit 132 electrically coupled to a regulation circuit 138. In some embodiments, power recovery circuit 132 can be configured to receive and process the electrical signal generated by ultrasonic transducer circuit 106. In some embodiments, power recovery circuit 132 can include a rectifying circuit (e.g., an active rectifier) to convert the electrical signal in an AC form to a DC form where the converted electrical signal may be associated with a first voltage (i.e., the supply voltage of the received ultrasonic waves).

In some embodiments, due to health hazards in propagating high-powered waves through biological tissue of the subject, government regulations may limit the amount of power (e.g., 720 mW/cm$^2$) provided by ultrasonic waves transmitted by interrogator 102. Therefore, the first voltage derived from the received ultrasonic waves may not be high enough to operate the electronic components of implantable device 104. For example, transistors used in complementary metal-oxide-semiconductor (CMOS) technology may require a minimum of about 2 Volts to operate the transistors.

In some embodiments, to provide a higher first voltage to operate the electronic components implantable device 102, the powering ultrasonic waves can be transmitted as a pulse width modulated (PWM) signal. In some embodiments, by transmitting the powering ultrasonic waves as the PWM signal, interrogator 102 can be configured to provide short, high intensity pulses such that the average intensity stays within the regulation limits and to provide higher instantaneous power to generate a higher first voltage. In some embodiments, the interrogator can be configured to control an instantaneous intensity and/or a pulse width (e.g., example ultrasonic wave settings) of the PWM signal to control the power provided by the powering ultrasonic waves.

In some embodiments, to enable implantable device 104 to be powered by these ultrasonic waves, power conveyor circuit 134 can include a charge pump configured to convert the first voltage to a second voltage greater than the first voltage. In some embodiments, the charge pump can include a plurality of coupled capacitors controlled by one or more switches to generate the second voltage. In some embodiments, the charge pump can achieve conversion gains of at least 1×, 2×, 3×, or 4×. In some embodiments, the magnitude of the second voltage can be controlled based on a switching frequency of the one or more switches.

As discussed above, power provided by the received ultrasonic waves can be inconsistent due to a host of factors including, for example, an implant depth of implantable device 104 or intervening biological material between ultrasonic transducer 108 and the ultrasonic wave source, e.g., interrogator 102. Accordingly, in some embodiments, to provide more consistent power to implantable device 104, power recovery circuit 132 can include an energy storage device 136 coupled to power conveyor circuit 134. In some embodiments, the energy storage device includes a battery or a storage capacitor. In some embodiments, to retain the small form factor of implantable device 104, the energy storage device can be configured as a storage capacitor.

In some embodiments, the storage capacitor can have a capacitance that is at least 0.1 μF, at least 0.25 μF, at least 0.5 μF, at least 1 μF, at least 2 μF, at least 4 μF, or at least 8. In some embodiments, the storage capacitor can have a capacitance that is less than 10 μF, less than 8 μF, less than 4 μF, less than 2 μF, less than 1 μF, less than 0.5 μF, or less than 0.25 μF. For example, the storage capacitor may have a capacitance in the range of 0.1-10 μF such as in the range of 0.5-2 μF. In some embodiments, the storage capacitor can have a capacitance that is about 1 μF.

In some embodiments, energy storage device 136 can be configured to operate in at least two power modes to enable implantable device 104 to more efficiently utilize power of received ultrasonic waves and to provide more consistent power. In some embodiments, the power modes include a charging mode in which a portion of power of the received ultrasonic waves can be conveyed to energy storage device 136 capable of storing the energy. In some embodiments, power conveyor circuit 134 can be configured to charge energy storage device 136 based on the generated first voltage. In some embodiments, the power modes include a discharging mode in which a portion of energy stored at energy storage device 136 is discharged to convey power from energy storage device 136 to provide additional power to other device components (e.g., stimulation circuit 114, detection circuit 116, or controller circuit 120, etc.) of implantable device 104. In some embodiments, the power flow to and from energy storage device 136 can be routed through power conveyor circuit 134.

In some embodiments, regulation circuit 138 can be configured to regulate the output voltage (e.g., the second voltage) generated by power conveyor circuit 134 to provide regulated voltages to one or more circuit loads of implantable device 104. In some embodiments, where power conveyor circuit 134 includes a charge pump, regulation circuit 138 can be configured to remove or reduce potential voltage ripples caused by operating switches of the charge pump. In some embodiments, regulation circuit 138 includes a DC voltage regulator (e.g., a low-dropout (LDO) regulator) to regulate a voltage supplied to digital circuit loads of implantable device 104. In some embodiments, regulation circuit 138 includes a DC voltage regulator (e.g., a low-dropout (LDO) regulator) to regulate a voltage supplied to digital circuit loads of implantable device 104. In some embodiments, regulation circuit 138 includes an AC voltage regulator (e.g., a low-dropout (LDO) regulator) to regulate a voltage supplied to analog circuit loads of implantable device 104.

In some embodiments, modulation and demodulation circuit 112 can include a demodulation circuit configured to demodulate the electrical signal generated by ultrasonic transducer circuit 106 to extract information encoded in the received ultrasonic waves. In some embodiments, the demodulation circuit can transmit the extracted information including an instruction to controller circuit 120 configured to control how implantable device 104 operates based on the instruction.

In some embodiments, to enable implantable device 104 to wireless communicate information with interrogator 102, modulation and demodulation circuit 112 can include a modulation circuit configured to encode the information using ultrasonic backscatter. This information is generated by implantable device 104 and, for ease of explanation, will sometimes be referred to as device information in the following descriptions.

In general, when implantable device 104 is embedded within a subject, the ultrasonic waves (including carrier waves) emitted by an ultrasonic transceiver of interrogator 102 will pass through biological tissue before being received by ultrasonic transducer circuit 106 of implantable device 104. As described above, the carrier waves cause mechanical vibrations on ultrasonic transducer 108 (e.g., a bulk piezoelectric transducer) to generate a voltage across ultrasonic transducer 108, which then imparts an electrical current to flow to the rest of implantable device 104. In some embodiments, the electrical current flowing through ultrasonic transducer 108 causes ultrasonic transducer circuit 106 to emit backscatter ultrasonic waves corresponding to the received ultrasonic waves.

In some embodiments, the modulation circuit can be configured to modulate the electrical current flowing through ultrasonic transducer 108 to encode the device information, which causes the resulting ultrasonic backscatter waves to also encode the device information. Accordingly, the ultrasonic backscatter emitted from implantable device 104 can encode the device information related to implantable device 104. In some embodiments, the modulation circuit can include one or more switches, such as an on/off switch or a field-effect transistor (FET). An example FET that may be used with some embodiments of implantable device 104 includes a metal-oxide-semiconductor field-effect transistor (MOSFET). In some embodiments, the modulation circuit can be configured to alter the impedance of an electrical current flowing through ultrasonic transducer 108, and variation in the flowing electrical current flowing encodes the information.

As will be further described below with respect to FIG. 2, the ultrasonic backscatter can be received by interrogator 102 and deciphered to extract the device information encoded in the ultrasonic backscatter, according to some embodiments. In some embodiments, the ultrasonic backscatter can be received by an interrogator that may be the same or different than interrogator 102 that transmitted the ultrasonic waves received by ultrasonic transducer 108.

In some embodiments, detection circuit 116 can be configured to interface with one or more sensors 140A-C to measure or detect one or more physiological conditions of the subject. In some embodiments, detection circuit 116 can include a driver configured to provide current to the one or more sensors 140A-C and receive generated signals from the one or more sensors 140A-C. In some embodiments, a received signal can include information representative of a detected physiological condition or representative of a measured physiological condition. In some embodiments, detection circuit 116 can be configured to transmit the information to controller circuit 120.

In some embodiments, one or more of sensors 140A-C can be located inside implantable device 104 or coupled to the exterior of implantable device 104. In some embodiments, implantable device 104 includes at least two sensors 140A-C. In some embodiments, the one or more physiological conditions can include temperature, pH, pressure, heart rate, strain, oxygen tension, a presence of an analyte, or an amount of the analyte. For example, the analyte may be oxygen or glucose.

In some embodiments, sensors 140A-C can include an optical sensor. In some embodiments, the optical sensor comprises a light source and an optical detector. In some embodiments, the optical sensor detects blood pressure or a pulse. In some embodiments, the optical sensor comprises a matrix comprising a fluorophore or luminescent probe, and wherein fluorescence intensity or fluorescence lifetime of the fluorophore depends on the amount of the analyte. In some embodiments, the optical sensor is configured to perform near-infrared spectroscopy. In some embodiments, the optical sensor detects glucose.

In some embodiments, sensors 140A-C can include a potentiometric chemical sensor or an amperometric chemical sensor. In some embodiments, the sensor detects oxygen, pH, or glucose.

In some embodiments, sensors 140A-C can include a temperature sensor. In some embodiments, the temperature sensor is a thermistor, a thermocouple, or a proportional to absolute temperature (PTAT) circuit.

In some embodiments, sensors 140A-C can include a pressure sensor. In some embodiments, the pressure sensor is a microelectromechanical system (MEMS) sensor. In some embodiments, detection circuit 116 is configured to measure blood pressure or a pulse.

In some embodiments, sensors 140A-C can include a strain sensor.

In some embodiments, detection circuit 116 can be configured to interface with, for example, sensor 140C to detect an electrophysiological signal from a nerve or a targeted subset of nerve fibers within the nerve, as will be further explained below with respect to FIG. 8. In some embodiments, sensor 140C can include electrode pads, which may be the same or different from electrode pads 142 operated by stimulation circuit 114. In some embodiments, detection circuit 116 can be configured to record neural activity of a nerve or the targeted subset of nerve fibers based on the detected electrophysiological signal.

In some embodiments, one or more techniques such as computational modeling (e.g., finite element models), inverse source estimation, multipole (e.g., tripole) neural recording, velocity-selective recording, or beamforming can be implemented by detection circuit 116 (alone or in conjunction with controller circuit 120) to selectively target the subset of nerve fibers. See, for example, Taylor et al., *Multiple-electrode nerve cuffs for low-velocity and velocity selective neural recording*, Medical & Biological Engineering & Computing, vol. 42, pp. 634-643 (2004); and Wodlinger et al., *Localization and Recovery of Peripheral Neural Sources with Beamforming Algorithms*, IEEE Transactions on Neural Systems and Rehabilitation Engineering, vol. 17, no. 5, pp. 461-468 (2009).

In some embodiments, detection circuit 116 can be configured to operate the plurality of electrodes of sensor 140C for targeted detection of the electrophysiological signal. For example, sensor 140C may be a curved member that extends from implantable device 104, as further described below with respect to FIG. 8. In some embodiments, detection circuit 116 can analyze the electrophysiological signal detected by all or a subset of the electrode pads to determine the subset of nerve fibers within the nerve that are transmitting the electrophysiological signal. Certain nerves may transmit compound electrophysiological signal (or compound action potentials), which is the sum of the electrophysiological signals (or action potentials) simultaneously transmitted by two or more different subsets of nerve fibers. Based on the electrophysiological signal detected by the plurality of electrode pads, detection circuit 116 may be able to determine which subset of nerve fibers transmits which electrophysiological signal. In some embodiments, data received from interrogator 102 (such as temperature data, or data related to an analyte concentration or other physiological condition) is further used to determine which subset of nerve fibers transmits the electrophysiological signal.

For example, in some embodiments, detection circuit 116 may be configured to selectively detect an electrophysiological signal from a targeted subset of nerve fibers using velocity-selective recording, which may be combined with multipolar (e.g., tripolar) recording (which can include any number of tripoles within the plurality of electrodes on one or more curved members).

Beamforming can additionally or alternatively be used to detect the electrophysiological signals from the targeted subset of nerve fibers. A portion of or all of the electrode pads of one or more curved members can detect the electrophysiological signal from the nerve, and detection circuit 116 can determine the cross-sectional location of the transmitted signal within the nerve based on the differences in electrophysiological signal detected by a portion or all of the electrode pads of the one or more curved members.

In some embodiments, stimulation of one or more nerves at a location separate from the location of implantable device 104 can result in a modulation of the electrophysiological signal at the location of implantable device 104. The modulation of the electrophysiological signal detected at different subsets of nerve fibers within the nerve in electrical communication with the electrode pads (e.g., electrode pads 142) of implantable device 104 can be the result of stimulation in different distant nerves. For example, stimulation of the splenic nerve can result in modulation of an electrophysiological signal detected from first subset of nerve fibers within the vagus nerve, and stimulation of a renal nerve can result in modulation of an electrophysiological signal detected from a second subset of nerve fibers within the vagus nerve. Therefore, an implantable device positioned on the vagus nerve can detect an electrophysiological signal from the first subset of nerve fibers to monitor stimulation of the splenic nerve, and a second subset of nerve fibers to monitor stimulation of the renal nerve.

In some embodiments, stimulation circuit 114 can be configured to emit a targeted electrical pulse to a subset of nerve fibers within the nerve by selectively activating one or more electrode pads 142 connected to the subset of nerve fibers. In some embodiments, implantable device 104 can include one or more curved members that electrically connect stimulation circuit 114 to electrode pads 142, as will be further described below with respect to FIG. 8.

In some embodiments, stimulation circuit 114 can be controlled by controller circuit 120 to operate electrode pads 142 or to selectively activate electrode pads 142. Selective activation can include, for example, activating a portion of electrode pads within the plurality of electrode pads 142 of one or more curved members and/or differentially activating all or a portion of the electrode pads within the plurality of electrode pads 142 of the one or more curved members. The plurality of electrodes can therefore be operated to steer the electrical pulse emitted by the plurality of electrode pads 142 to the target subset of nerve fibers. Techniques such as electrical field interference or multipolar stimulation (e.g., tripolar stimulation) can be used to target the electrical pulse to the subset of nerve fibers within the nerve, according to some embodiments. See, for example, Grossman, et al., *Noninvasive Deep Brain Stimulation via Temporally Interfering Electrical Fields*, Cell, vol. 169, pp. 1029-1041 (2017). Electrode pads 142 within one or more curved members can be selectively activated by controller circuit 120 to target the emitted electrical pulse to the subset of nerve fibers.

The subset of nerve fibers targeted by the emitted electrical pulse can be the same or different as the subset of nerve fibers from which the electrophysiological signal is detected by detection circuit 116. The one or more curved member configured to emit the targeted electrical pulse can be the same or different as the one or more curved members on implantable device 104 configured to detect the electrophysiological signal. The emitted targeted electrical pulse can stimulate the nerve at the position of implantable device 104. The subset of nerve fibers targeted by the electrical pulse can be the same or a different subset of nerve fibers for which the electrophysiological signal is selectively detected.

The subset of nerve fibers targeted by the electrical pulse emitted by implantable device 104 can be, for example, one or more (e.g., 2, 3, 4, or more) fascicles, or a portion of one or more (e.g., 2, 3, 4, or more) fascicles within the nerve. In some embodiments, the subset of nerve fibers comprises or consists of afferent nerve fibers within the nerve, or a subset of afferent nerve fibers within the nerve. In some embodiments, the subset of nerve fibers comprises or consists of efferent nerve fibers within the nerve, or a subset of efferent nerve fibers within the nerve. In some embodiments, the subset of nerve fibers comprises or consists of efferent nerve fibers within two or more fascicles within the nerve or afferent nerve fibers within two or more fascicles within the nerve.

Targeted stimulation of a subset of nerve fibers by emitting a targeted electrical pulse to the subset of nerve fibers can result in stimulation of a nerve at a location distant from the position of the nerve. The distant nerve stimulated by implantable device 104 depends on the subset of nerves at the position of implantable device 104 targeted by the electrical pulse emitted by the device. In some embodiments, implantable device 104 is positioned at a first nerve locus and is configured to stimulate a second nerve locus by emitting a targeted electrical pulse to a subset of nerve fibers within the first nerve locus that is associated with the second nerve locus. In some embodiments, the first nerve locus and the second nerve locus are separated by one or more nerve branch points or one or more synapses. In some embodiments, the second nerve locus is proximal to the brain relative to the first nerve locus, and in some embodiment the second nerve locus is distal from the brain relative to the first nerve locus. In some embodiments, the targeted subset of nerve fibers comprises or consists of afferent nerve fibers. In some embodiments, the targeted subset of nerve fibers comprises or consists of efferent nerve fibers.

In some embodiments, controller circuit 120 includes a command processor 122, a power monitor 124, a mode detector 126, and a memory 150. In some embodiments, memory 150 includes a non-transitory storage memory such as register memory, a processor cache, or Random Access Memory (RAM). In some embodiments, controller circuit 120 can be a digital circuit, an analog circuit, or a mixed-signal integrated circuit. Examples of controller circuit 120 may include a microprocessor, a finite state machine (FSM), a field programmable gate array (FPGA), and a microcontroller.

In some embodiments, mode detector 126 can be configured to determine an operating mode command from the ultrasonic waves received by ultrasonic transducer 108. In some embodiments, mode detector 126 can determine the operating mode command upon determining a correspondence to a pattern from a plurality of predetermined patterns 156 stored in memory 150. For example, the pattern may be a sequence of one or more pulses having specific ultrasonic wave properties such as an ultrasound pulse duration. In this example, mode detector 126 can match a portion of the operating mode command to one or more of predetermined patterns 156 to determine a matching pattern. In another example, the pattern may correspond to an ultrasound property such as a pulse duration, an amplitude, or a phase or frequency change. In this example, mode detector 126 may analyze the ultrasound property (e.g., the pulse duration) of the portion to determine a correspondence to a pattern. In some embodiments, the portion of the operating mode command can be a single pulse that indicates the start of the operating mode command. In other embodiments, the portion can be a sequence of ultrasound pulses. In some embodiments, controller circuit 120 can be configured to perform methods 600A-B of FIGS. 6A-B, respectively, to determine the operating mode command, as will be further described below.

In some embodiments, mode detector 126 can receive the ultrasonic waves as an electrical signal that has been generated (e.g., demodulated) by modulation and demodulation circuit 112 based on the ultrasonic waves received in ultrasonic transducer circuit 106. In some embodiments, mode detector 126 can include one or more detection circuits configured to detect one or more ultrasonic wave properties from the electrical signal. In some embodiments, one of these detection circuits can include a zero-crossing circuit configured to determine a pulse duration of each ultrasound pulse in the operating mode command. For example, the zero-crossing circuit can be configured to count and store a number of instances that a first portion of the electrical signal crosses a predefined voltage level within a predetermined number of clock cycles to determine a pulse duration. In some embodiments, the predefined voltage level is a voltage close to 0 V (e.g., less than 10 mV, less than 50 mV, less than 100 mV, or less than 200 mV).

In some embodiments, command processor 122 can be configured to set an operating mode of implantable device 104 to one operating mode from a plurality of predetermined operating modes 152 based on the operating mode command determined by mode detector 126, as will be further described below with respect to FIGS. 6A-B. In some embodiments, command processor 122 can store the received operating mode command and associated instructions in memory 150 such as an instruction register. In some embodiments, command processor 122 can be configured to control implantable device 104 to enter an operating state corresponding to the operating mode based on the stored operating mode command. For example, command processor 122 may be implanted as a FSM or a program in a microcontroller that controls the operating states of implantable device 104 based on a current operating state and one or more detected inputs such as one or more received operating mode commands, one or more sensor values, or a combination thereof.

In some embodiments, command processor 122 can be configured to extract information from a portion of the operating mode command to configure various parameters or to select an operating mode. Information encoded in the ultrasonic waves emitted by the interrogator and received by the closed-loop implantable device can include, for example, instructions for starting or stopping neuromodulation, one or more calibration instructions, one or more updates to the operation software, and/or or one or more templates (such as template electrophysiological signals, one or more template electrophysiological signals, and/or one or more template stimulation signals). In some embodiments, command processor 122 can be configured to process and store the received instructions in memory 150. In some embodiments, command processor 122 can enter an operating mode from a plurality of operating modes based on one or more received operating mode commands, as will be further described below with respect to FIGS. 6A-B. In some embodiments, the plurality of operating modes can include, for example, a mode to stimulate a nerve, a mode to record neural activity, or a mode to determine one or more physiological conditions, as will be further described below with respect to FIGS. 7-8. For example, if the operating mode command indicates that implantable device 104 should enter the neural stimulation mode, controller circuit 120 may be configured to control stimulation circuit 114 to stimulate specific nerve fibers or portions of the nerve.

In some embodiments, when command processor 122 controls implantable device 104 to enter the neural activity recording mode or a mode to determine one or more physiological conditions, command processor 122 may control detection circuit 116 to retrieve the device information (e.g., neural record or detected/measured physiological condition). In some embodiments, command processor 122 can be configured to retrieve command 154 associated with a current operating mode 152 to control operations of implantable device 104. For example, in the neural activity recording mode, command processor 122 may receive command 154 corresponding to the neural activity recording mode and issue command 154 to control detection circuit 116 to sample a neural activity (e.g., an example of device information) of a nerve. In some embodiments, upon retrieving the device information, command processor 122 can be configured to control modulation and demodulation circuit 112 based on command 154 to encode the device information in an ultrasonic backscatter, as described above.

In some embodiments, to provide power controls and calibration to implantable device 104, power monitor 124 can be configured to monitor an available power and a power consumption of implantable device 104. In some embodiments, the available power can include a supply power provided by the ultrasonic waves received at ultrasonic transducer 108 and include an accessible power stored on implantable device 104. For example, the accessible power may include power accessible from energy storage device 136 storing excess energy. In some embodiments, power monitor 124 can determine the power consumption based on an output voltage generated by power conveyor circuit 134.

In some embodiments, when command processor 122 controls implantable device to enter a power calibration mode, command processor 122 can be configured to generate information indicating whether more power or less power should be transmitted to implantable device 104 based on the available power and the consumed power monitored by power monitor 124. For example, command processor 122 can receive commands 154 corresponding to operating mode 152 (e.g., power calibration mode) that are transmitted to other components such as power monitor 124 and modulation and demodulation circuit 112 to generate and transmit the power information. In some embodiments, controller circuit 120 can be configured to control modulation and demodulation circuit 112 according to command 154 to encode the generated information in an ultrasonic backscatter.

Figure 2:
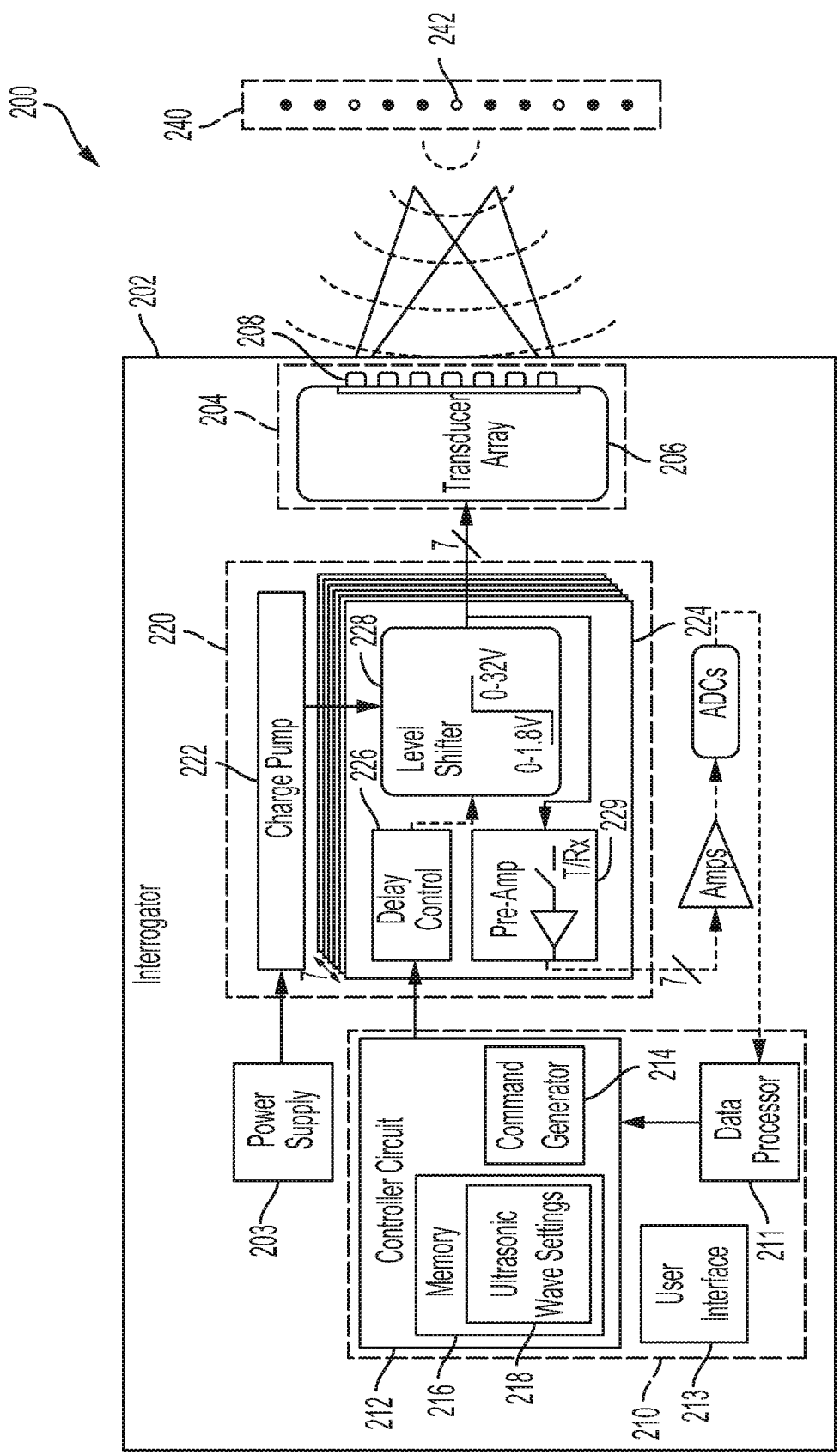
FIG. 2 illustrates a system including an interrogator configured to operate one or more implantable devices using ultrasonic waves, according to some embodiments.

FIG. 2 illustrates a system 200 including an interrogator 202 configured to operate one or more implantable devices 240 using ultrasonic waves, according to some embodiments. In some embodiments, interrogator 202 can be an example of interrogator 102 as described above with respect to FIG. 1.

In some embodiments, interrogator 202 includes a power supply 203, a computational circuit 210, a signal-generation circuit 220, and an ultrasonic transducer circuit 204. As shown, power supply 203 can be configured to power computational circuit 210 and signal-generation circuit 220. In some embodiments, power supply 203 can provide 1.8V, although any suitable voltage can be used. For example, power supply 203 may include one or more batteries to supply the 1.8V.

In some embodiments, signal-generation circuit 220 includes a charge pump 222 configured to power one or more channels 224. In some embodiments, charge pump 222 can be configured to increase the voltage provided by power supply 203. For example, charge pump 222 may increase the 1.8V supplied by power supply 203 to 32V.

In some embodiments, each channel 224 is coupled to and controls an operation of a corresponding ultrasonic transducer 208 of transducer circuit 204. In some embodiments, ultrasonic transducer 208 connected to channel 224 can be configured only to receive or only to transmit ultrasonic waves, in which case switch 229 can be optionally omitted from channel 224. In some embodiments, each channel 224 can include the following electronic components: a delay control 226, a level shifter 228, and a switch 229.

In some embodiments, delay control 226 can be configured to control the waveforms and/or signals of ultrasonic waves transmitted by ultrasonic transducer 208. In some embodiments, delay control 226 can control, for example, a phase shift, a time delay, a pulse frequency, a wave shape (including amplitude and wavelength), or a combination thereof based on commands from controller circuit 212 to generate the transmit waveform. In some embodiments, the data representing the wave shape and frequency for each channel can be stored in a 'wave table' stored in delay control 226 or in memory 216. This may allow the transmit waveform on each channel 224 to be different.

In some embodiments, delay control 226 can be connected to a level shifter 228 that is configured to shift input pulses from delay control 226 to a higher voltage used by ultrasonic transducer 208 to transmit the ultrasonic waves. In some embodiments, delay control 226 and level shifter 228 can be configured to be used to stream data to the actual transmit signals to transducer array 206. In some embodiments, the transmit waveform for each channel 224 can be produced directly by a high-speed serial output of a microcontroller or other digital system and sent to the transducer element (e.g., ultrasonic transducer 208) through level shifter 228 or a high-voltage amplifier.

In some embodiments, switch 229 of channel 224 can configure a corresponding ultrasonic transducer 208 to receive ultrasonic waves such as an ultrasonic backscatter. In some embodiments, the received ultrasonic waves are converted to an electrical current by ultrasonic transducer 208 (set in a receiving mode) and transmitted to data processor 211 to process data captured in the received ultrasonic waves. In some embodiments, an amplifier, an analog-to-digital converter (ADC), a variable-gain-amplifier, or a time-gain-controlled variable-gain-amplifier which compensates for tissue loss, and/or a band pass filter can be included to process the received ultrasonic waves.

In some embodiments, channel 224 described above does not include a T/Rx switch 229, but instead contains independent Tx (transmit) and Rx (receive) with a high-voltage Rx (receiver circuit) in the form of a low noise amplifier with good saturation recovery. In some embodiments, the T/Rx circuit includes a circulator. In some embodiments, transducer array 206 includes more transducer elements (e.g., ultrasonic transducer 208) than processing channels 224, and interrogator 202 can be configured to include a multiplexer to select different sets of transmitting elements for each pulse. For example, 64 transmit/receive channels may be connected via a 3:1 multiplexer to 192 physical transducer elements—with only 64 transducer elements active on a given pulse.

In some embodiments, computational circuit 210 can be a digital circuit, an analog circuit, or a mixed-signal integrated circuit. Examples of computational circuit 210 may include a microprocessor, a finite state machine (FSM), a field programmable gate array (FPGA), and a microcontroller. In some embodiments, interrogator 202 can include a volatile memory, which can be accessed by computational circuit 210.

In some embodiments, computational circuit 210 includes controller circuit 212, data processor 211, and user interface 213. In some embodiments, controller circuit 212 includes command generator 214 and memory 216 storing ultrasonic wave settings 218.

In some embodiments, command generator 214 can be configured to generate instructions to control operation of delay control 226 to transmit one or more operating mode commands to one or more implantable devices 240 to operate the one or more implantable devices 240. In some embodiments, as will be further described below with respect to FIG. 6B, the operating mode command can instruct an implantable device (e.g., implantable device 242) receiving the operating mode command to upload certain device data or to download data encoded in the operating mode command. Examples of such operating mode commands and their waveform formats are further described below with respect to FIGS. 5A-C.

In some embodiments, the device data received and processed by data processor 211 can include power information. In these embodiments, command generator 214 can be configured to set or select ultrasonic wave settings to control an output power of transmitted ultrasound waves based on the device information received from, for example, implantable device 242. For example, received device information may indicate that more power should be transmitted to implantable device 242. In this example, command generator 214 may select ultrasonic wave settings 218, such as a higher pulse width or a higher instantaneous intensity, of the waveform to increase power of ultrasonic waves transmitted by ultrasonic transducer circuit 204.

In some embodiments, transducer circuit 204 includes one or more ultrasonic transducers 208 configured to transmit ultrasonic waves to power implantable devices 240 such as implantable device 242. In some embodiments, as shown in FIG. 2, transducer circuit 204 includes transducer array 206 having a plurality of ultrasonic transducers 208. In some embodiments, transducer array 206 includes 1 or more, 2 or more, 3 or more, 5 or more, 7 or more, 10 or more, 15 or more, 20 or more, 25 or more, 50 or more, 100 or more 250 or more, 500 or more, 1000 or more, 2500 or more, 5000 or more, or 10,000 or more ultrasonic transducers. In some embodiments, transducer array 206 includes 100,000 or fewer, 50,000 or fewer, 25,000 or fewer, 10,000 or fewer, 5000 or fewer, 2500 or fewer, 1000 or fewer, 500 or fewer, 200 or fewer, 150 or fewer, 100 or fewer, 90 or fewer, 80 or fewer, 70 or fewer, 60 or fewer, 50 or fewer, 40 or fewer, 30 or fewer, 25 or fewer, 20 or fewer, 15 or fewer, 10 or fewer, 7 or fewer or 5 or fewer ultrasonic transducers. Transducer array 206 may be, for example, a chip comprising 50 or more ultrasonic transducer pixels.

As shown in FIG. 2, transducer circuit 204 includes a single transducer array 206; transducer circuit 204, however, can include 1 or more, 2 or more, or 3 or more separate transducer arrays, according to some embodiments. In some embodiments, transducer circuit 204 includes 10 or fewer transducer arrays (such as 9, 8, 7, 6, 5, 4, 3, 2, or 1 transducer arrays). In some embodiments, the separate transducer arrays can be placed at different points of a subject, and can communicate to the same or different implantable devices 240. In some embodiments, the transducer arrays can be located on opposite sides of an implantable device such as implantable device 242.

In some embodiments, the specific design of transducer array 206 of interrogator 202 depends on the desired penetration depth, aperture size, and size of the individual ultrasonic transducers 208 within transducer array 206. The Rayleigh distance, R, of the transducer array 206 is computed as:

$$R = \frac{D^2 - \lambda^2}{4\lambda} \approx \frac{D^2}{4\lambda}, D^2 \gg \lambda^2$$

where D is the size of the aperture and X is the wavelength of ultrasound in the propagation medium (i.e., the tissue). As understood in the art, the Rayleigh distance is the distance at which the beam radiated by transducer array 206 is fully formed. That is, the pressure filed converges to a natural focus at the Rayleigh distance to maximize the received power. Therefore, in some embodiments, implantable devices 240 can be approximately the same distance from transducer array 206 as the Rayleigh distance.

The individual ultrasonic transducers 208 in transducer array 206 can be modulated to control the Raleigh distance and the position of the beam of ultrasonic waves emitted by transducer array 206 through a process of beamforming or beam steering. Techniques such as linearly constrained minimum variance (LCMV) beamforming can be used to communicate a plurality of implantable devices 240 (e.g., implantable device 242) with an external ultrasonic transceiver. See, for example, Bertrand et al., Beamforming Approachesfor Untethered, Ultrasonic Neural Dust Motes for Cortical Recording: a Simulation Study, IEEE EMBC (August 2014). In some embodiments, beam steering is performed by adjusting the power or phase of the ultrasonic waves emitted by ultrasonic transducers 208 in transducer array 206.

In some embodiments, interrogator 202 (e.g., computational circuit 210) includes one or more of instructions for beam steering ultrasonic waves using one or more ultrasonic transducers 208, instructions for determining the relative location of one or more implantable devices 240, instructions for monitoring the relative movement of one or more implantable devices 240, instructions for recording the relative movement of one or more implantable devices 240, and instructions for deconvoluting backscatter from a plurality of implantable devices 240.

In some embodiments, user interface 213 can be configured to allow a user (e.g., a physician or a patient) to control the operations of interrogator 202 to power or operate implantable devices 240 or to communicate with implantable devices 240. In some embodiments, user interface 213 can include an input device that provides input, such as a touch screen or monitor, keyboard, mouse, or voice-recognition device to interrogator 202. In some embodiments, user interface 213 can include an output device such as any suitable device that provides output, such as a touch screen, monitor, printer, disk drive, or speaker.

In some embodiments, interrogator 202 can be controlled using a separate computer system (not shown), such as a mobile device (e.g., a smartphone or a tablet). The computer system can wirelessly communicate to interrogator 202, for example through a network connection, a radiofrequency (RF) connection, or Bluetooth. The computer system may, for example, turn on or off interrogator 202 or analyze information encoded in ultrasonic waves received by interrogator 202.

In some embodiments, interrogator 202 communicates with a plurality of implantable devices 240. This can be performed, for example, using multiple-input, multiple output (MIMO) system theory. For example, communication between interrogator 202 and the plurality of implantable devices 240 may be performed using time division multiplexing, spatial multiplexing, or frequency multiplexing. Interrogator 202 can receive a combined ultrasonic backscatter from the plurality of the implantable devices 240, which can be deconvoluted, thereby extracting information from each implantable device 242. In some embodiments, interrogator 202 can be configured to focus the ultrasonic waves transmitted from transducer array 206 to a particular implantable device through beam steering. For example, interrogator 202 may focus the transmitted ultrasonic waves to a first implantable device (e.g., implantable device 242), receives backscatter from the first implantable device, focuses transmitted ultrasonic waves to a second implantable device, and receives backscatter from the second implantable device. In some embodiments, interrogator 202 transmits ultrasonic waves to a plurality of implantable devices 240, and then receives ultrasonic backscatter from the plurality of implantable devices 240.

In some embodiments, interrogator 202 or one or more of ultrasonic transducers 208 are wearable. For example, interrogator 202 or one or more of ultrasonic transducers 208 may be fixed to the subject's body by a strap or adhesive. In another example, interrogator 202 can be a wand, which may be held by a user (such as a healthcare professional). In some embodiments, interrogator 202 can be held to the body via suture, simple surface tension, a clothing-based fixation device such as a cloth wrap, a sleeve, an elastic band, or by sub-cutaneous fixation. In some embodiments, one or more ultrasonic transducers 208 or transducer array 206 of interrogator 202 may be positioned separately from the rest of interrogator 202. For example, transducer array 206 may be fixed to the skin of a subject at a first location (such as proximal to one or more implanted devices), and the rest of interrogator 202 may be located at a second location, with a wire tethering ultrasonic transducer 208 or transducer array 206 to the rest of interrogator 202.

Figure 3:
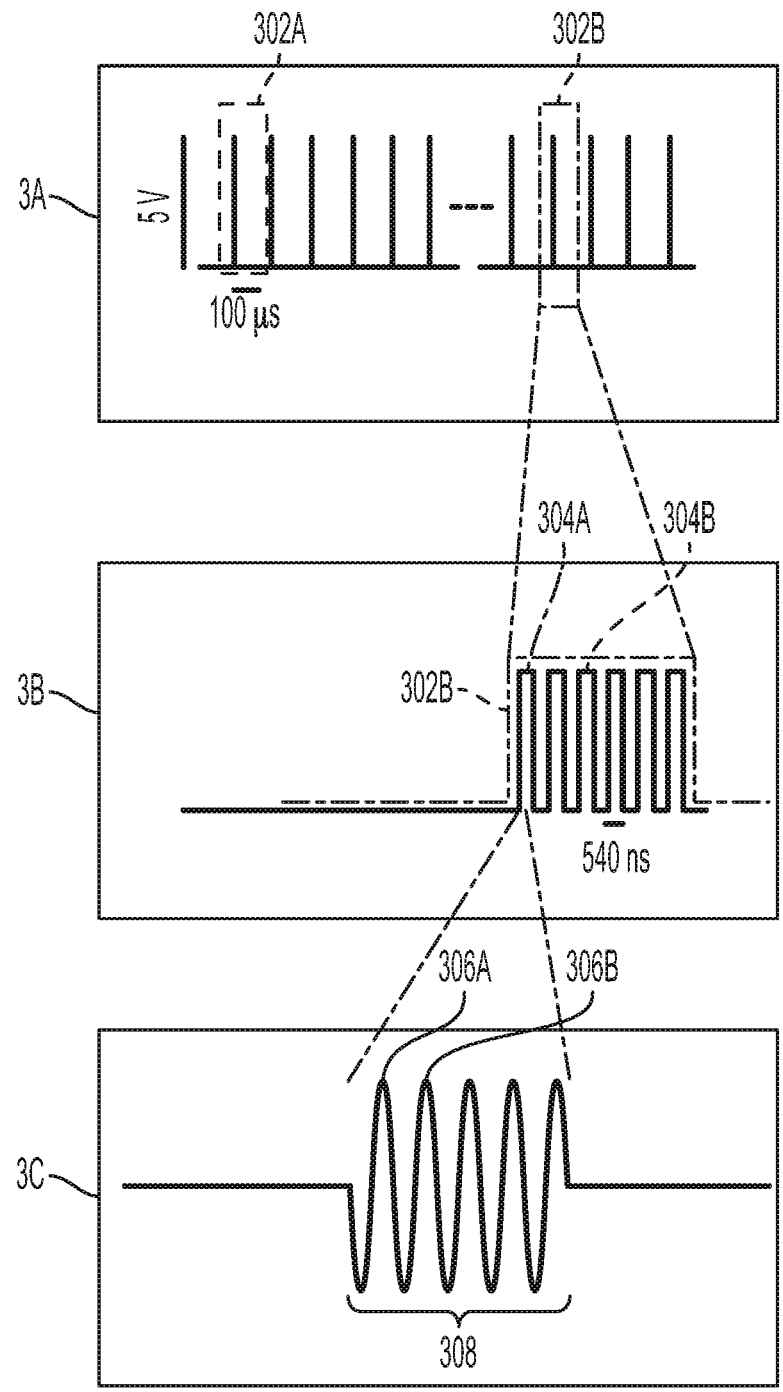
FIG. 3 illustrates panels showing portions of emitted ultrasonic waves for operating an implantable device, according to some embodiments.

FIG. 3 illustrates panels 3A-C showing portions of emitted ultrasonic waves for operating an implantable device, according to some embodiments. For example, the ultrasonic waves shown in panels 3A-C may be emitted by interrogator 102 of FIG. 1 or interrogator 202 of FIG. 2. In some embodiments, the emitted ultrasonic waves can be configured to be emitted by one or more other implantable devices.

Panel 3A shows that the emitted ultrasonic waves include a series of ultrasonic wave commands such as ultrasonic wave commands 302A and 302B. In some embodiments, each of the ultrasonic wave commands may include one or more pulses of ultrasonic waves (i.e., also known as ultrasound pulses). For example, panel 3B shows a zoomed-in view of ultrasonic wave command 302B, which may include a sequence of six ultrasound pulses (e.g., pulses 304A-B). For illustration purposes only, the amplitude (i.e., pressure amplitude) and pulse width (i.e., also called pulse length or pulse duration) of each pulse in ultrasonic wave command 302B is shown as being the same, but, this may not be the case. In some embodiments, the amplitude or pulse width of each ultrasound pulse may be dictated by the ultrasonic wave protocol implemented by the interrogator. Therefore, the amplitudes and pulse width of the pulses may be different. In some embodiments, each of the ultrasound pulses may include one or more carrier cycles (i.e., also known as vibration or oscillation cycles). As used in the present disclosure herein, a carrier cycle may correspond to a single oscillation of the ultrasonic waves. For example, panel 3C shows a zoomed-in view of ultrasound pulse 304A that includes five carrier cycles (e.g., ultrasound cycles 306A-B) that comprise a pulse duration 308 of ultrasound pulse 304A.

Figure 4:
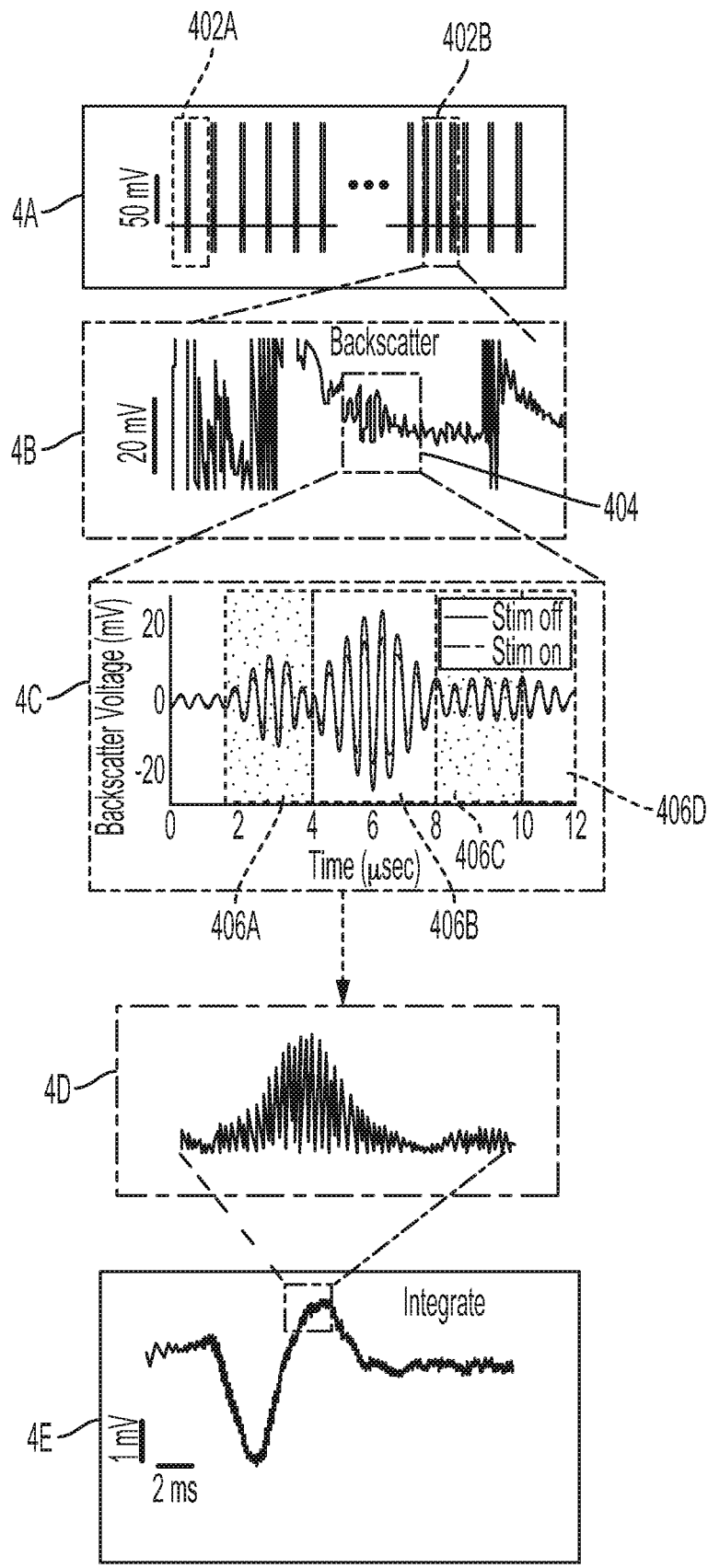
FIG. 4 illustrate panels showing how an interrogator processes an ultrasonic backscatter received at the interrogator, according to some embodiments.

FIG. 4 illustrates panel 4A-E showing how an interrogator processes an ultrasonic backscatter received at the interrogator, according to some embodiments. In some embodiments, an implantable device (e.g., implantable device 104 of FIG. 1) can be configured to emit the ultrasonic backscatter, as shown in panel 4A, in response to receiving ultrasonic waves such as those described above with respect to panel 3A of FIG. 3.

Panel 4A shows the ultrasonic backscatter received from the implantable device. In some embodiments, the ultrasonic backscatter can correspond to a backscatter of the ultrasonic waves transmitted to the implantable device, as shown in panel 3A of FIG. 3. As shown in panel 4A, the ultrasonic backscatter can include backscattered portions 402A-B that corresponds to a backscatter of the operating mode command portions of the transmitted ultrasonic waves of panel 3A. In some embodiments, at the end of a transmit cycle, the interrogator can be configured to control a switch (e.g., switch 229) to disconnect the transmit module and connect the receive module to receive the ultrasonic backscatter.

Panel 4B shows a zoomed-in view of a backscatter of a single ultrasonic pulse 404, which can be analyzed to extract data encoded in the backscatter 404. For example, as shown in panel 4C, the ultrasonic backscatter 404 can be filtered. As shown in panel 4C, the filtered backscatter can include four distinct regions 406A-D corresponding to reflections arising from mechanical boundaries: region 406A corresponds to reflection from the biocompatible material that encapsulates the implantable device: region 406B correspond to reflection from the top surface of the miniaturized ultrasonic transducer: (3) region 406C correspond to reflection from the boundary between a printed circuit board and the miniaturized ultrasonic transducer; and region 406D correspond to reflection from the back of the printed circuit board of the implantable device. The amplitude of the backscatter waves reflected from the surface of the miniaturized transducer changed as a function of changes in impedance of the current returning to the miniaturized ultrasonic transducer, and can be referred to as the "responsive backscatter" since this region of the backscatter encodes information generated at the implantable device. For example, panel 4C shows the difference in amplitude of the filtered backscatter depending on whether the implantable device is in an operating mode for stimulating a nerve. Further analysis of the filtered backscatter may include rectifying the ultrasonic backscatter, as shown in panel 4D, and integrating the rectified signal to decode data, as shown in panel 4E.

Figure 5A:
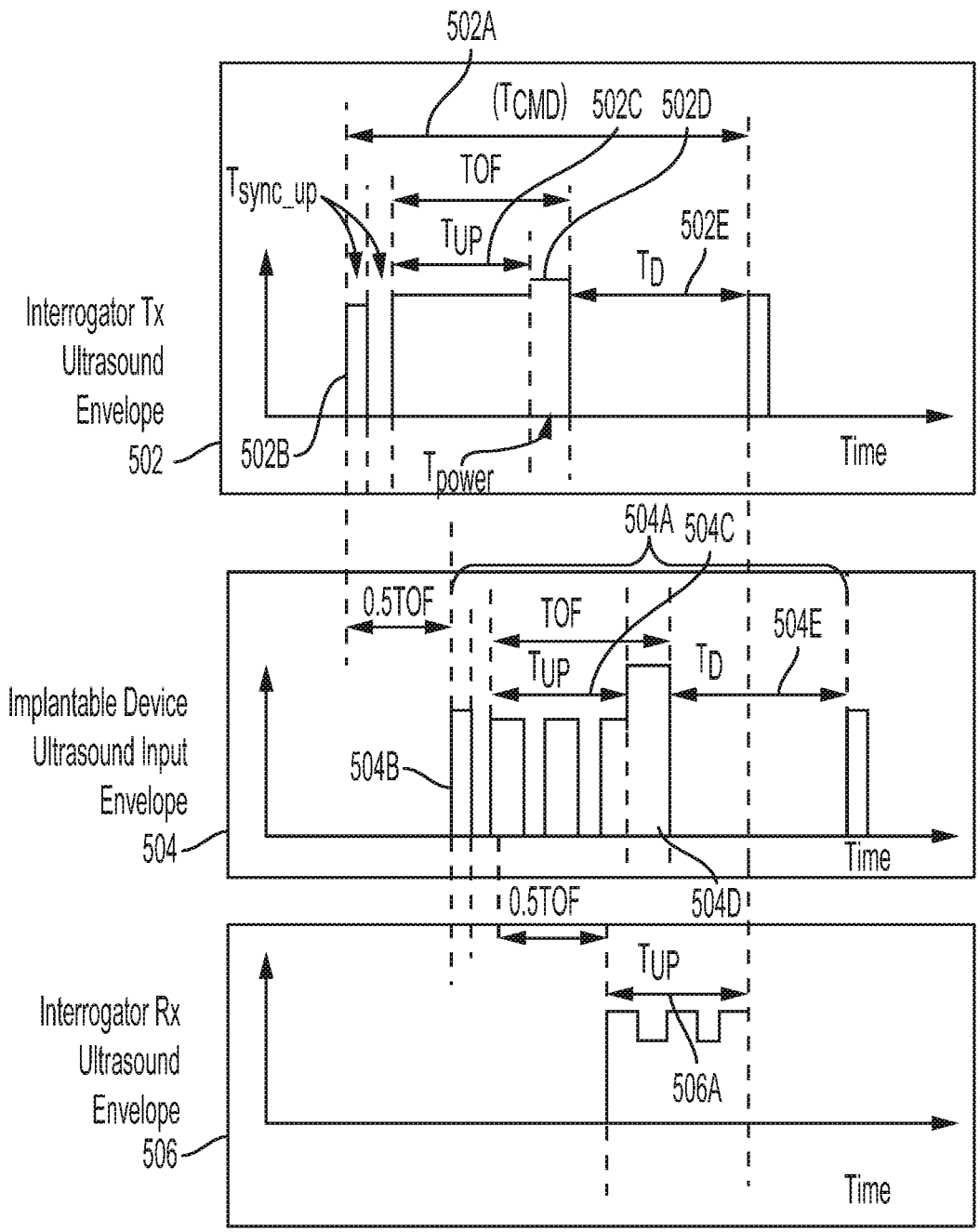
FIG. 5A, FIG. 5B, and FIG. 5C illustrate panels showing ultrasonic waves encoding operating mode commands, according to some embodiments.
Figure 5B:
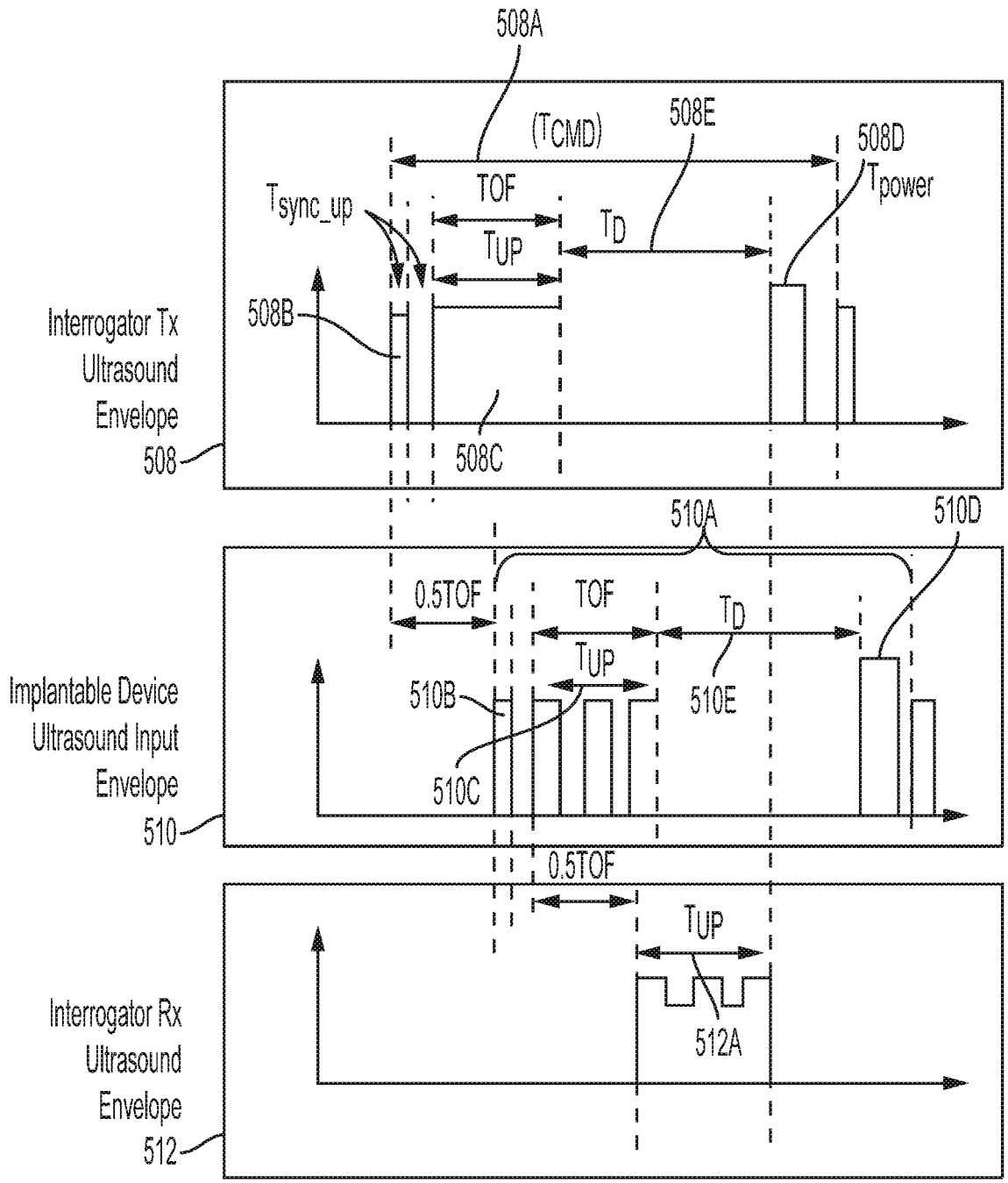
Figure 5C:
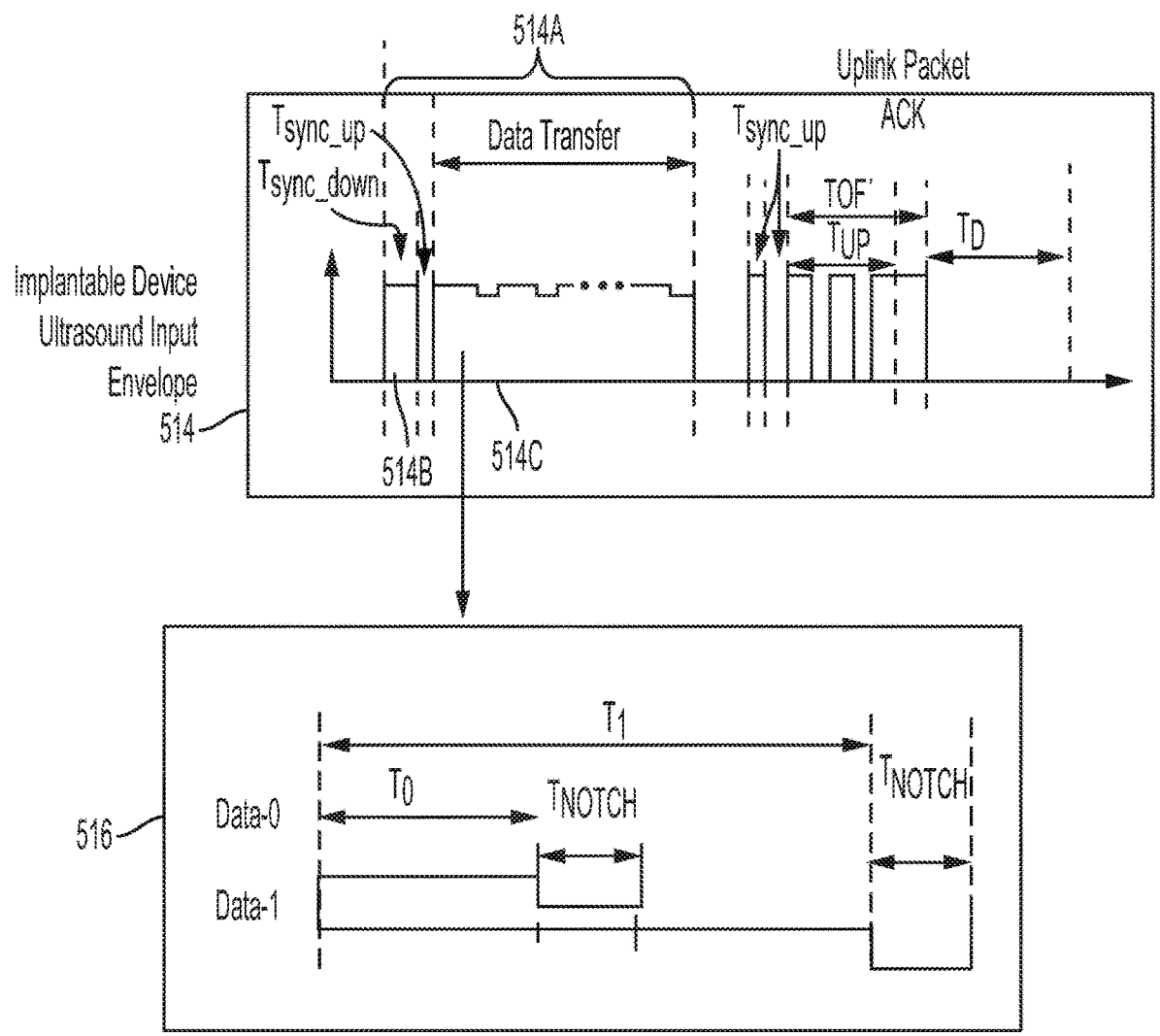

FIGS. 5A-C illustrate panels showing ultrasonic waves encoding operating mode commands, according to some embodiments.

In ultrasound communications, the time of flight (TOF) refers to the two way travel time between an interrogator transmitting the ultrasonic waves and an implantable device receiving the ultrasonic waves. The time of flight may depend on the distance of the interrogator relative to implantable device. In some embodiments, the time of flight may constrain how an operating mode command is generated because data uplink is enabled by encoding information in a backscatter of the ultrasonic waves. Accordingly, if the interrogator transmits carrier waves while previously transmitted ultrasonic waves are backscattered, there may be crosstalk between the transmitted carrier waves and the ultrasonic backscatter.

FIG. 5A illustrates panel 502-506 showing the timing requirements and data structure of an operating mode command associated with data uplink, according to some embodiments. Panel 502 shows an example ultrasound envelope for the operating mode command 502A transmitted by an ultrasound interrogator (e.g., interrogator 102 or interrogator 202). Operating mode command 502A can have a total time or period of $T_{cmd}$ and include a first portion 502B having a pulse duration of $T_{sync\_up}$ p, a second portion 502C having a duration of $T_{up}$, a third portion 502D having a duration of $T_{power}$, and a fourth portion 502E having a duration of $T_D$.

First portion 502B may include a first pulse of operating mode command 502A that enables a mode detector of the implantable device to determine a type of operating mode command. In some embodiments, the mode detector can be configured to determine that the pulse duration of first portion 502B corresponds to an uplink pattern of $T_{sync\_up}$ to determine that operating mode command 502A is associated with uplink. The uplink pattern may be associated with a carrier frequency of the received ultrasonic waves. For example, $T_{sync\_up}$ may be a multiple of the carrier frequency.

In some embodiments, using the pulse duration of first portion 502B to differentiate between operating mode commands 502A can allow the implantable device to operate in multiple operating modes as well as to be powered using ultrasonic waves as an adjustable PWM signal. As discussed above with respect to FIG. 1, transmitting ultrasonic waves as the PWM signal can enable the implantable device to be sufficiently powered using ultrasonic waves while controlling the average intensity of the ultrasonic waves to stay within government regulations. The use of the PWM signal with varying pulse widths, however, would render traditional communication protocol approaches using defined timing structures ineffective. This is in part because the pulse width of the PWM signal can be dynamically adjusted based on power needs of the implantable device, so the absence or presence of carrier waves at specific time intervals may not necessary indicate any instructions or commands. The use of the first portion 502B, as described above, addresses the problems that would be encountered using traditional approaches for communication protocols.

Second portion 502C may include communication ultrasonic waves that enable the implantable device to upload device data and the duration of $T_{up}$ corresponds to the time that the implantable device has to modulate the carrier wave to upload device data. Third portion 502D of duration $T_{power}$ correspond to ultrasonic waves that can be used by, for example, the implantable device 104 to power its various components such as power conveyor circuit 134 or energy storage device 136. Finally, fourth portion 502E can correspond to a dead time of $T_D$ where no carrier waves are transmitted. During fourth portion 502E, the interrogator can be configured to enter a receive mode to allow for receipt of an ultrasonic backscatter. In some embodiments, the total duration of the second and third portions 502C-D is configured to remain within the time of flight such that crosstalk does not occur. In some embodiments, the dead time can be at least as long as $T_{up}$, but may be longer depending on how much power needs to be provided by third portion 502D.

As described above, the mode detector can be configured to analyze a duration of the third portion to determine whether the ultrasonic waves are associated with power transmission. In some embodiments, a duration of pulses in third portion 502C that exceeds the uplink pattern (e.g., $T_{sync\_up}$) and that exceeds a downlink pattern (e.g., $T_{sync\_down}$) can indicate that power is to be extracted from the ultrasonic waves.

Panel 504 shows an ultrasound envelop for operating mode command 502A received at the implantable device. As shown, the implantable device can receive operating mode command 502A as operating mode command 504A after a period of time (i.e., half of TOF) that operating mode command 502A was transmitted. The received operating mode command 504A includes portions 504B-E that correspond to portions 502B-E of operating mode command 502A, as described above. Panel 506 shows an ultrasonic backscatter of second portion 504C received at the interrogator. As shown, the ultrasonic backscatter would have a duration of $T_{up}$ and needs to be received during the dead time of fourth portion 502E to ensure that crosstalk does not occur so that the interrogator can successfully extract data from the ultrasonic backscatter.

FIG. 5B illustrates panels 508-512 showing the timing requirements and data structure of an operating mode command associated with data uplink, according to some embodiments. Panel 508 shows an example ultrasound envelope for the operating mode command 508A transmitted by an ultrasound interrogator (e.g., interrogator 102 or interrogator 202). Operating mode command 508A can have a total time or period of $T_{cmd}$ and include a first portion 508B having a pulse duration of $T_{sync\_up}$, a second portion 508C having a duration of $T_{up}$, a third portion 508D having a duration of $T_{power}$, and a fourth portion 508E having a duration of $T_D$. In contrast to operating mode command 502A as shown in FIG. 5A, third portion 508D including powering ultrasonic waves can be transmitted after the dead time of fourth portion 508E. In some embodiments, this configuration enables the duration of $T_{up}$ to be extended and for ultrasonic wave transmissions after the first portion 508B to stay within a duration of the time of flight. Accordingly, if the power needs of the implantable device requires that the duration of $T_{power}$ to increase such that the combined duration of the second and third portions 502C-D (as shown in panel 502) exceeds the time of flight, then the powering ultrasonic waves can be configured to be transmitted after the dead time.

Panel 510 shows an ultrasound envelop for operating mode command 508A received at the implantable device. As shown, the implantable device can receive operating mode command 508A as operating mode command 510A after a period of time (i.e., half of time of flight) that operating mode command 508A was transmitted. The received operating mode command 510A includes portions 510B-E that correspond to portions 508B-E of operating mode command 508A, as described above. Panel 512 shows an ultrasonic backscatter of second portion 510C received at the interrogator. As shown, the ultrasonic backscatter would have a duration of $T_{up}$ and needs to be transmitted during the dead time of fourth portion 508E to ensure that crosstalk does not occur so that the interrogator can successfully extract data form the ultrasonic backscatter.

FIG. 5C illustrates panels 514-516 showing the timing requirements and data structure of an operating mode command associated with data downlink, according to some embodiments. Panel 514 shows an example ultrasound envelope for the operating mode command 514A received by an ultrasound interrogator (e.g., interrogator 102 or interrogator 202). Operating mode command 514A can have a total time or period of $T_{cmd}$ and include a first portion 514B having a pulse duration of $T_{sync\_down}$ and a second portion 514C having a duration of $T_{data\_tranfser}$. In some embodiments, the mode detector can be configured to determine that the pulse duration of first portion 514B corresponds to $T_{sync\_down}$ associated with data downlink. In some embodiments, the value of $T_{sync\_down}$ can be different than $T_{sync\_up}$, but less than the value for $T_{power}$. For example, $T_{sync\_up}$ down can be set to a first multiple of the carrier frequency (e.g., $T_{sync\_down}=5*T_c$) and $T_{sync\_up}$ can be set to a second multiple of the carrier frequency (e.g., $T_{sync\_up}=T_c$). In some embodiments, a pulse duration that exceeds $T_{sync\_down}$ and $T_{sync\_up}$ can configure the implantable device to extract power from the ultrasonic waves (e.g., $T_{power}>5*T_c$).

In some embodiments, upon determining that first portion 514B indicates the downlink mode, the implantable device can be configured to extract data from second portion 514C. In some embodiments, data can be encoded in second portion 514C using pulse-width modulated amplitude-shift keying (PWM-ASK) encoding scheme. For example, as shown in panel 516, a pulse encoding logical 0 can have a higher amplitude than a pulse encoding logical 1. Additionally, the pulse encoding logical 0 may have a waveform with period $T_0$ (e.g., $T_0=10*T_c$) following by $T_{notch}$ (e.g., $T_{notch}=5*T_c$), whereas the pulse encoding logical 1 may have a waveform with period $T_1$ (e.g., $T_1=15*T_c$) following by $T_{notch}$ (e.g., $T_{notch}=5*T_c$). The use of PWM-ASK may ensure that sufficient power is transmitted in portion 514C if multiple data values of logical 0 are transmitted in a sequence. In some embodiments, data can be encoded in operating mode command 514A using another encoding scheme such as pulse-interval encoding (PIE), frequency-shift keying (PSK), or phase-shift keying (PSK).

Figure 6A:
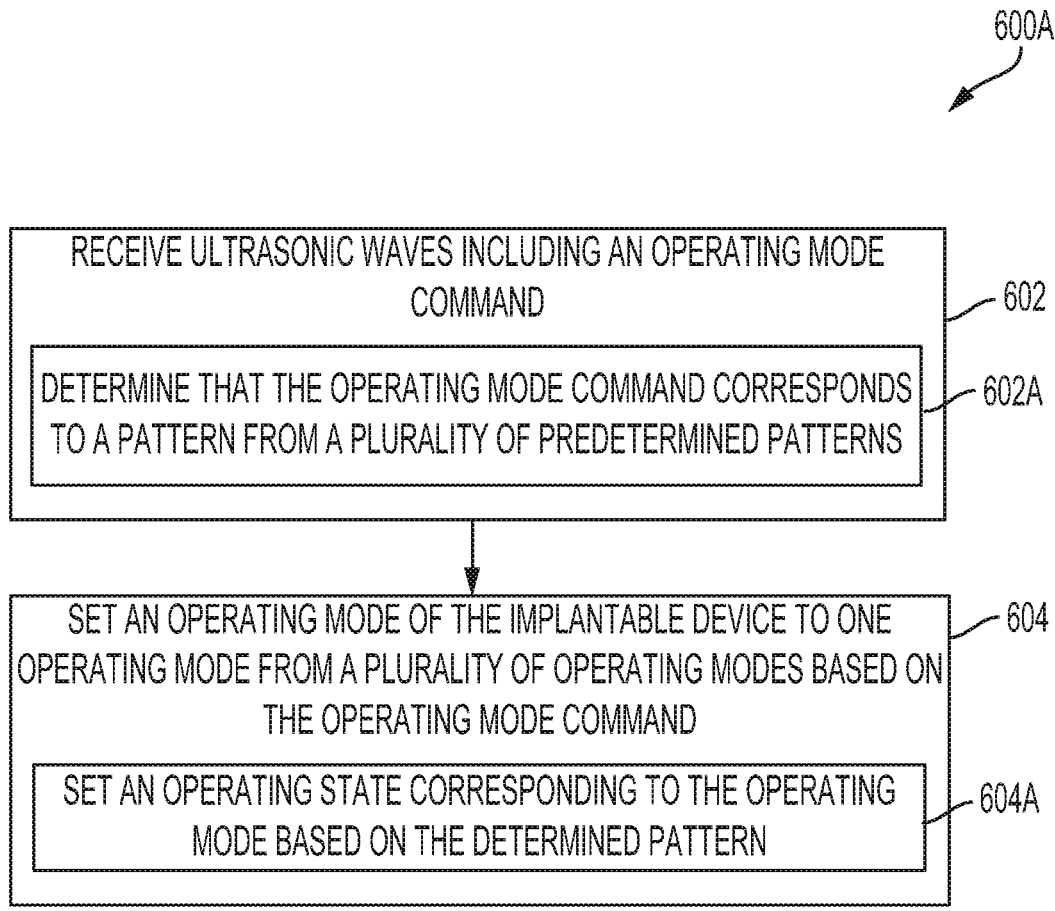
FIG. 6A and FIG. 6B illustrate methods for operating an implantable device using ultrasonic waves, according to some embodiments.

FIG. 6A illustrates a method 600A for operating an implantable device using ultrasonic waves, according to some embodiments. In some embodiments, the implantable device may be an example of implantable device 104 of FIG. 1. For ease of explanation, various steps below of method 600 may refer to components of implantable device 104 as described with respect to FIG. 1.

In step 602, the implantable device receives ultrasonic waves including an operating mode command. In some embodiments, an ultrasonic transducer (e.g., ultrasonic transducer 108) of the implantable device can be configured to receive the ultrasonic waves and convert energy from the received ultrasonic waves into an electrical signal including an electrical representation of the operating mode command. In some embodiments, the ultrasonic waves are transmitted by an interrogator such as interrogator 102 of FIG. 1 or interrogator 202 of FIG. 2. In some embodiments, the ultrasonic waves can be transmitted by another implantable device. In some embodiments, the operating mode command can correspond to one or more pulses of the ultrasonic waves, as described above with respect to panel 3B of FIG. 3. In some embodiments, step 602 includes step 602A.

In step 602A, the implantable device determines that the operating mode command corresponds to a pattern from a plurality of predetermined patterns. In some embodiments, the implantable device can be configured to determine the correspondence by determining a correspondence between a first portion of the operating mode command and the pattern. For example, the implantable device may compare the first portion with one or more patterns from the plurality of predetermined patterns to determine the correspondence. In some embodiments, the first portion can include a single pulse of the operating mode command. For example, the first portion may be the initial pulse of the operating mode command. In some embodiments, the first portion can include a sequence of two or more pulses of the operating mode command.

In some embodiment, the plurality of predetermined patterns can be a plurality of corresponding pulses with different properties. In some embodiments, the plurality of predetermined patterns can be a plurality of corresponding values associated with a property of a pulse. For example, a pulse property may include a pulse duration, a pulse amplitude, or a phase or frequency change. In some embodiments, each predetermined pattern of the plurality of patterns can include a unique set of values corresponding to two or more pulse properties. In some embodiments, each predetermined pattern of the plurality of patterns can include a unique sequence of pulses.

In some embodiments, the plurality of predetermined patterns includes a plurality of corresponding pulse durations, as described above with respect to FIG. 1. In some embodiments, one or more of the pulse durations are predetermined based on a carrier signal period of the received ultrasonic waves.

In some embodiments, a mode detector (e.g., mode detector 126) of the implantable device can be configured to count a number of instances that a first portion of the electrical signal crosses a predefined voltage level to determine whether the operating mode command corresponds to the pattern. In some embodiments, the predefined voltage level may be a voltage value close to 0 V (e.g., less than 10 mV, less than 50 mV, less than 100 mV, or less than 200 mV). In some embodiments, the number of instances may correspond to a pulse duration of the operating mode command.

In some embodiments, the mode detector can be configured to continuously monitor the ultrasonic waves to determine whether an operating mode command is received. For example, the mode detector may determine that the operating command is received if a first portion of the operating mode command is determined to correspond to a pattern from the plurality of predetermined patterns.

In step 604, the implantable device sets an operating mode of the implantable device to one operating mode from a plurality of predetermined operating modes based on the operating mode command. In some embodiments, the operating mode may include a stimulation mode, a neural-activity recording mode, or a sensor mode, as described above with respect to FIG. 1. In some embodiments, setting the operating mode may include step 604A.

In step 604A, the implantable device sets an operating state corresponding to the operating mode based on the determined pattern. In some embodiments, the implantable device can be configured to implement and maintain operation logic that includes a plurality of operating states and transitions defined between operating states. In some embodiments, a controller circuit (e.g., controller circuit 120) of the implantable device can be configured to implement and maintain the operation logic as to set the operating state based on the determined pattern. In some embodiments, the controller circuit can include a finite state machine (FSM) to implement the operation logic. In some embodiments, the controller circuit can include a microprocessor to implement the operation logic. In other embodiments, the controller circuit can be implemented using a field programmable gate array (FPGA) or a microcontroller.

In some embodiments, the implantable device can be configured to maintain a current operating state and transition the implantable device from the current operating state i to a next operating state based on the operating mode command. In some embodiments, the implantable device can be configured to operate according to the next operating state, which becomes the new current operating state. For example, the implantable device can control one or more of its components based on one or more commands associated with the set operating mode. In some embodiments, associations between the plurality of operating states (e.g., operating mode 152) and a plurality of corresponding commands (e.g., command 154) can be stored in the memory (e.g., memory 150).

In some embodiments, as described above with respect to step 602, the mode detector can be configured to continuously monitor received ultrasonic waves to determine whether an operating mode command is received. In these embodiments, the implantable device can be configured to reset the operating based on the detected operating mode command.

Figure 6B:
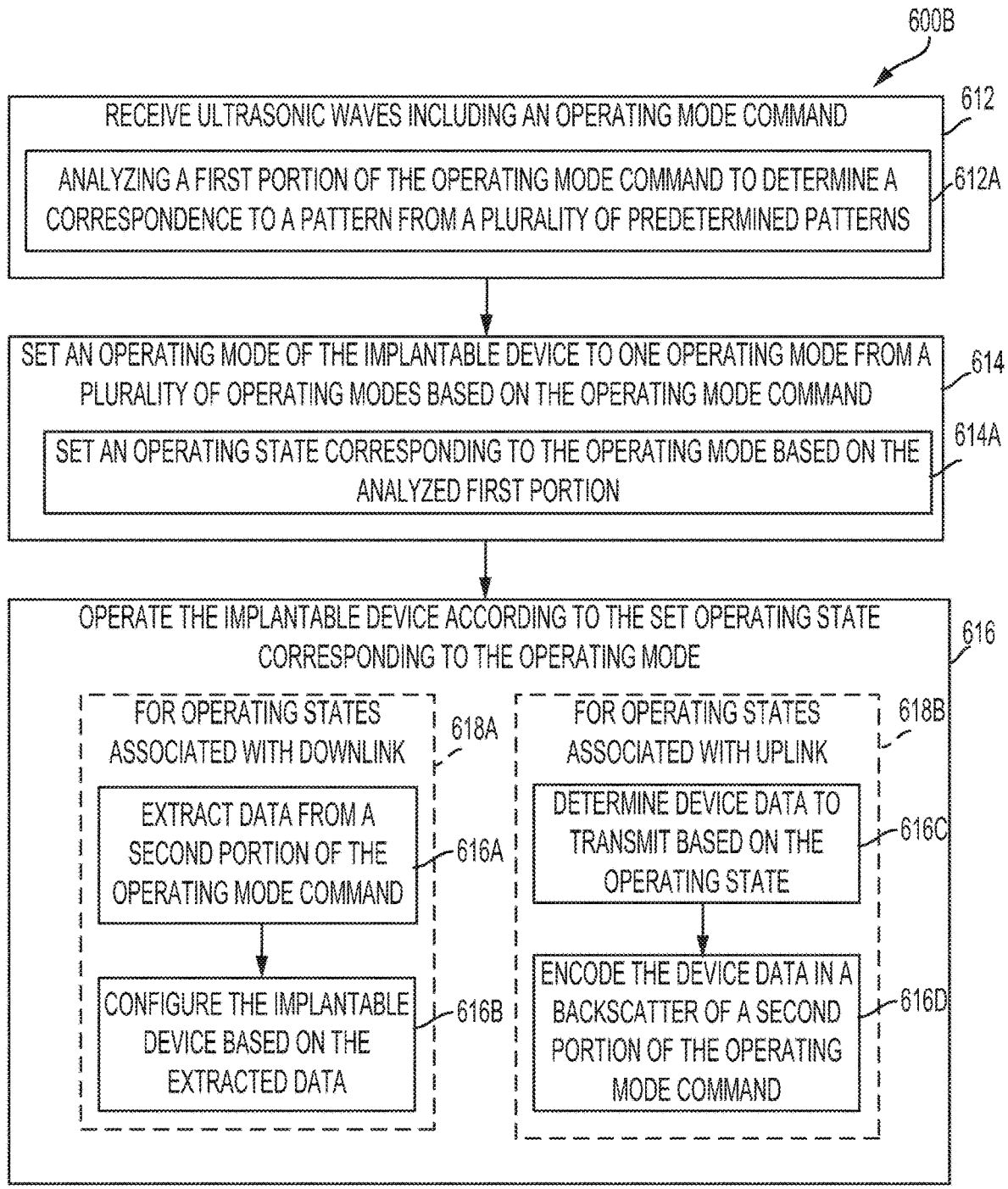

FIG. 6B illustrates a method 600B for operating an implantable device using ultrasonic waves, according to some embodiments. In some embodiments, the implantable device may be an example of implantable device 104 of FIG. 1. For ease of explanation, various steps below of method 600 may refer to components of implantable device 104 as described with respect to FIG. 1.

In step 612, the implantable device receives ultrasonic waves including an operating mode command. In some embodiments, step 612 corresponds to step 602 as described above with respect to FIG. 6A. In some embodiments, step 612 includes steps 612A, which may correspond to step 602A of FIG. 6A.

In step 612A, the implantable device analyzes a first portion of the operating mode command to determine a correspondence to a pattern from a plurality of predetermined patterns. In some embodiments, the implantable device determines that the operating mode command corresponds to the pattern in response to determining that the first portion corresponds to the determined pattern. For example, as described above with respect to step 602A, the first portion may be a single pulse that indicates a start of the operating mode command. In other examples, the first portion may include a sequence of two or more pulses of the operating mode command.

In step 614, the implantable device sets an operating mode of the implantable device to one operating mode from a plurality of predetermined operating modes based on the operating mode command. In some embodiments, the plurality of operating modes includes a downlink mode for downloading data from the received ultrasonic waves and includes an uplink mode for uploading data generated at the implantable device to an external device using the received ultrasonic waves of step 612. In some embodiments, the plurality of operating modes includes a plurality of downlink modes for performing different operations on downloaded data, as described above with respect to FIG. 1. In some embodiments, the plurality of operating modes includes a plurality of uplink modes for uploading different types of device to the interrogator, as described above with respect to FIG. 1.

In some embodiments, step 614 corresponds to step 604 as described above with respect to FIG. 6A. In some embodiments, step 614 includes steps 614A. In step 614A, the implantable device sets an operating state corresponding to the operating mode based on the analyzed first portion.

For example, the implantable device can set the operating state based on the determine pattern of step 612A. In some embodiments where the implantable device implements a FSM, data representing the correspondence to the determined pattern can be used as an input to the FSM to set the operating state.

In some embodiments, the determined correspondence to the pattern can configure the implantable device to set the operating mode to a downlink mode for extracting data from the received ultrasonic waves. For example, the implantable device may be configured to extract data from a second portion of the operating mode command. In some embodiments, the determined correspondence to the pattern can configure the implantable device to set the operating mode to an uplink mode for uploading device data to the interrogator using the received ultrasonic waves.

In step 616, the implantable device operates according to the set operating state corresponding to the operating mode. In some embodiments, step 616 includes one or more of steps 616A-D.

In some embodiments, for operating states associated with downlink 618A, step 616 includes steps 616A-B. In step 616A, the implantable device extracts data from a second portion of the operating mode command. In some embodiments, the second portion includes a sequence of one or more pulses of the operating mode command. In some embodiments, the second portion follows the first portion and does not overlap the first portion. In some embodiments, the implantable device can be configured to decode the second portion to extract the data. In some embodiments, the implantable device can be configured to decode the second portion using a pulse-width modulated amplitude-shift keying (PWM-ASK) encoding scheme. In some embodiments, the extracted data can include an instruction to select an operating mode. In some embodiments, the extracted data can include one or more parameters (e.g., a PGA gain) associated with recording neural activity. In some embodiments, the extracted data can include one or more parameters associated with stimulating a nerve.

In step 616B, the implantable device configures the implantable device based on the extracted data. In some embodiments, the implantable device can be configured to generate one or more commands to control one or more components based on the extracted data. In some embodiments, the one or more commands (e.g., command 154) are generated based on the current operating state as set in step 614A.

In some embodiments, for operating states associated with uplink 618B, step 616 includes steps 616C-D. In step 616C, the implantable device determines device data to transmit based on the operating state. In some embodiments, the device data includes data generated at the implantable device. In some embodiments, the implantable device can be configured to retrieve the device data from memory (e.g., memory 150) based on the operating state.

In some embodiments, the operating state can correspond to a physiological-condition reporting mode (i.e., an example of an uplink mode), in which the device data can include information associated with a physiological condition detected or measured by the implantable device in the physiological-condition reporting mode. For example, the physiological condition may include a temperature, a pulse rate, a blood pressure, a pH level, a presence of an analyte, or a concentration of the analyte. In some embodiments, the analyte can include oxygen or glucose.

In some embodiments, the operating state can correspond to a neural-activity reporting mode (i.e., an example of an uplink mode). In this operating state, the implantable device can be configured to generate device data including information associated with an electrophysiological signal detected by the implantable device in the neural-activity reporting mode, as will be further described below with respect to FIG. 8.

In some embodiments, the operating state can correspond to an acknowledgement mode (i.e., an example of an uplink mode), in which the device data can include an acknowledgement that the implantable device successfully extracted an operating instruction from previously-received ultrasonic waves.

In step 616D, the implantable device encodes the device data in a backscatter of a second portion of the operating mode command. As described above with respect to step 616A, the second portion can include a sequence of one or more pulses of the operating mode command. In some embodiments, the second portion follows the first portion and does not overlap the first portion. In some embodiments, the implantable device can be configured to modulate an electric current generated from the received ultrasonic waves of step 612 to encode the data. In some embodiments, one or more ultrasonic transducers of the implantable device can be configured to emit an ultrasonic backscatter of the ultrasonic waves, in which the backscattered ultrasonic wave encodes the device data.

Accordingly, based on method 600B, the implantable device can be configured to operate in an uplink mode or a downlink mode based on the operating mode command received in the ultrasonic waves.

Figure 7:
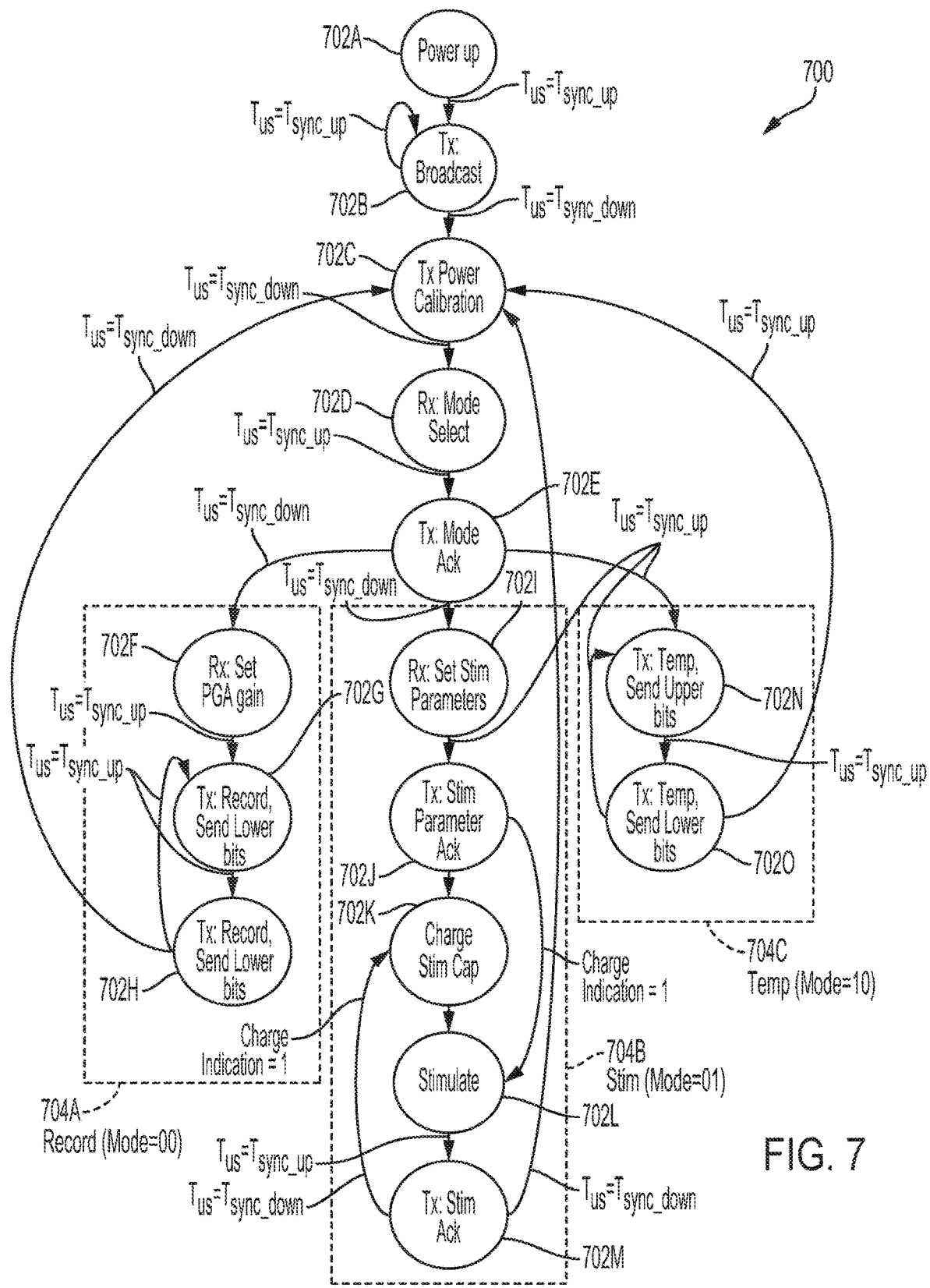
FIG. 7 illustrates a diagram showing example operating logic of an implantable device, according to some embodiments.

FIG. 7 illustrates a diagram 700 showing example operating logic of an implantable device (e.g., implantable device 104), according to some embodiments. As discussed above, a controller circuit (e.g., controller circuit 120) of the implantable device can be configured to implement a finite state machine (FSM) to control operations of the implantable device. For example, diagram 700 shows a Moore state machine. As shown in diagram 700, the FSM may include a plurality of operating states 702A-0. In some embodiments, the implantable device includes a plurality of operating modes, which may each correspond to a unique subset of the plurality of operating states 702A-0. While the FSM is shown as being a Moore machine, the implantable device can be configured its control the operating logic according to other types of FSMs. For example, instead of the Moore machine, the FSM may be implemented as a Mealy state machine, a Harel state machine, or a Unified Modeling Language (UML) state machine.

In some embodiments, the implantable device can be configured to transition from a current operating state to a next operating state based on the operating mode command in received ultrasonic waves, as described above with respect to FIGS. 6A-B. In some embodiments, the implantable device can be configured to compare information corresponding to the operating mode command to one or more patterns from a plurality of predetermined patterns to set the operating mode and associated operating state in the FSM. For example, as shown in diagram 700, the operating mode command can be associated with an ultrasound pulse duration (e.g., $T_{us}$) that can match an uplink pattern (e.g., a time period of $T_{sync\_up}$) or a downlink pattern (e.g., a time period of $T_{sync\_down}$). The uplink pattern may be associated with transitioning the implantable device to an operating state for uploading data and the downlink pattern may be associated with transitioning the implantable device to an operating state for downloading data.

In some embodiments, the implantable device can be configured to upload and download data through ultrasonic communications. While the following description may be described with respect to the implantable device communicating with an interrogator, it should be understood that the implantable device can similarly use ultrasonic waves to communicate with another implantable device, according to some embodiments. As described above with respect to FIG. 6B, whenever the implantable device transitions to an operating state associated with downlink of data, the implantable device can be configured to decode a portion of the ultrasonic waves received from an interrogator to extract an operating mode command for operating the implantable device. As described above with respect to FIG. 6B, whenever the implantable device transitions to an operating state associated with uplink of data, the implantable device can be configured to encode device data to be transmitted in a backscatter of a portion of the received ultrasonic waves. Then, the interrogator can be configured to receive the ultrasonic backscatter and decode the device data encoded in the ultrasonic backscatter.

In some embodiments, the implantable device can be configured to start in operating state 702A corresponding to a power-up operating mode. In operating state 702A, the implantable device can be configured to use the ultrasonic waves received at one or more ultrasonic transducers to charge one or more energy storage devices (e.g., energy storage device 136) of the implantable device.

In some embodiments, the implantable device can be configured to continuously monitor the received ultrasonic waves to determine whether an operating mode command is included in the received ultrasonic waves. As shown in diagram 700, when the operating mode command corresponds to the uplink pattern (i.e., $T_{us}=T_{syn\_up}$), the implantable device can transition to operating state 702B corresponding to a broadcast operating mode. In operating state 702B, the implantable device can transmit a device ID to the interrogator.

In some embodiments, the implantable device can be configured to retransmit the device ID in operating state 702B until a next operating mode command corresponding to the downlink pattern ((e.g., $T_{us}=T_{sync\_down}$) is detected. Then, the implantable device can transition to operating state 702C corresponding to a power calibration operating mode. In operating state 702C, the implantable device can transmit power information to the interrogator. For example, the power information may include an available power or a consumed power, as described above with respect to FIG. 1. In some embodiments, upon receiving the power information, the interrogator can be configured to adjust one or more ultrasonic wave settings (e.g., a power pulse intensity or a pulse width) based on the power information. Accordingly, power provided by the interrogator can be adjusted based on power information transmitted by the implantable device to the interrogator.

As shown in diagram 700, when a next operating mode command corresponds to the downlink pattern (i.e., $T_{us}=T_{sync\_down}$), the implantable device can transition from operating state 702C to operating state 702D corresponding to a mode selection operating mode. In operating state 702D, the implantable device can extract data from a second portion of the received operating mode command. In some embodiments, the extracted data may include information selecting an operating mode of the implantable device.

When a next operating mode command corresponds to the uplink pattern (i.e., $T_{us}=T_{sync\_up}$), the implantable device can transition from operating state 702D to operating state 702E corresponding to a mode-acknowledgement operating mode. In operating state 702E, the implantable device can transmit an acknowledgement to the interrogator indicating that the selection information associated with selecting an operating mode was successfully received.

When a next operating mode command corresponds to the uplink pattern (i.e., $T_{us}=T_{sync\_up}$), the implantable device can determine which of one or more reporting operating modes to enter based on the selection information previously received in operating state 702D. For example, the reporting operating modes may be associated with transmitting information associated with various physiological conditions such as a temperature, a pulse rate, a pH level, or a presence or a concentration of a specific analyte. For example, as shown in diagram 700, the implantable device may transition to operating state 702N corresponding to temperature operating mode 704C. In some embodiments, the amount of information that can be uploaded is limited (e.g., 4 bits of information). Therefore, as shown in diagram 700, temperature operating mode 704C may include multiple operating states 702N-O for transmitting a measured temperature. In some embodiments, when a next operating mode command corresponds to the downlink pattern (i.e., $T_{us}=T_{sync\_up}$), the implantable device may transition from operating state 702O back to operating state 702C to recalibrate power transmission from the interrogator.

Returning to operating state 702E, when a next operating mode command corresponds to the downlink pattern (i.e., $T_{us}=T_{sync\_down}$), the implantable device can determine whether to enter a neural-activity recording mode 704A or a neural-stimulation mode 704B based on the selection information previously received in operating state 702D.

In some embodiments, when the selection information indicates neural-activity recording mode 704A, the implantable device can transition from operating state 702E to operating state 702F of neural-activity recording mode 704A. In neural-activity recording mode 704A, the implantable device can be configured to receive parameters in operating state 702F and transmit neural-activity data in operating states 702G-H. For example, a parameter may include a programmable-gain amplifier (PGA) gain that configures the implantable device to control how much to amplify a detected neural activity signal. As described above with respect to temperature operating mode 704C, device data such as a neural-activity record may be too large to transmit in a backscatter of the second portion of the operating mode command. Accordingly, neural-activity recording mode 704A may include multiple operating states 702G-H for transmitting the entire neural-activity record. Further details for how the neural activity can be sampled and recorded are provided below with respect to FIG. 8. In some embodiments, when a next operating mode command corresponds to the downlink pattern (i.e., $T_{us}=T_{sync\_up}$), the implantable device may transition from operating state 702H back to operating state 702C to recalibrate power transmission from the interrogator.

In some embodiments, when the selection information indicates neural stimulation mode 704B, the implantable device can transition from operating state 702E to operating state 702I of neural stimulation mode 704B. In neural stimulation mode 704B and as shown in diagram 700, the implantable device can be configured to receive and stimulation parameters in operating state 702I and transmit an acknowledgement of the received parameters in operating state 702J based on successively received operating mode commands.

In operating state 702J, a charge detector of the implantable device can be configured to determine whether a stimulation capacitor is sufficiently charged to be used to stimulate a nerve. If the charge detector indicates sufficient charge (i.e., Charge Indication=1), the implantable device transitions to operating state 702L, otherwise the implantable device remains in operating state 702K in which the stimulation capacitor continues to be charged based on ultrasonic waves received from the interrogator. In operating state 702L, the implantable device can stimulate one or more selected nerves by emitting an electric pulse to the one or more selected nerves, as will be further described below with respect to FIG. 8.

When the operating mode command corresponds to an uplink pattern, the implantable device can transition to operating state 702M corresponding to an acknowledgement operating mode to transmit a status of the stimulation as performed in operating state 702L. When the operating mode command corresponds to a downlink pattern, the implantable device can transition back to operating state 702K to repeat stimulation or back to operating state 702C to recalibrate the implantable device to enter other operating modes depending on data included in the operating mode command. For example, an instruction extracted from the operating mode command may request repeated stimulation, which would cause the implantable device to transition to operating state 702K to recharge the stimulation capacitor.

Figure 8:
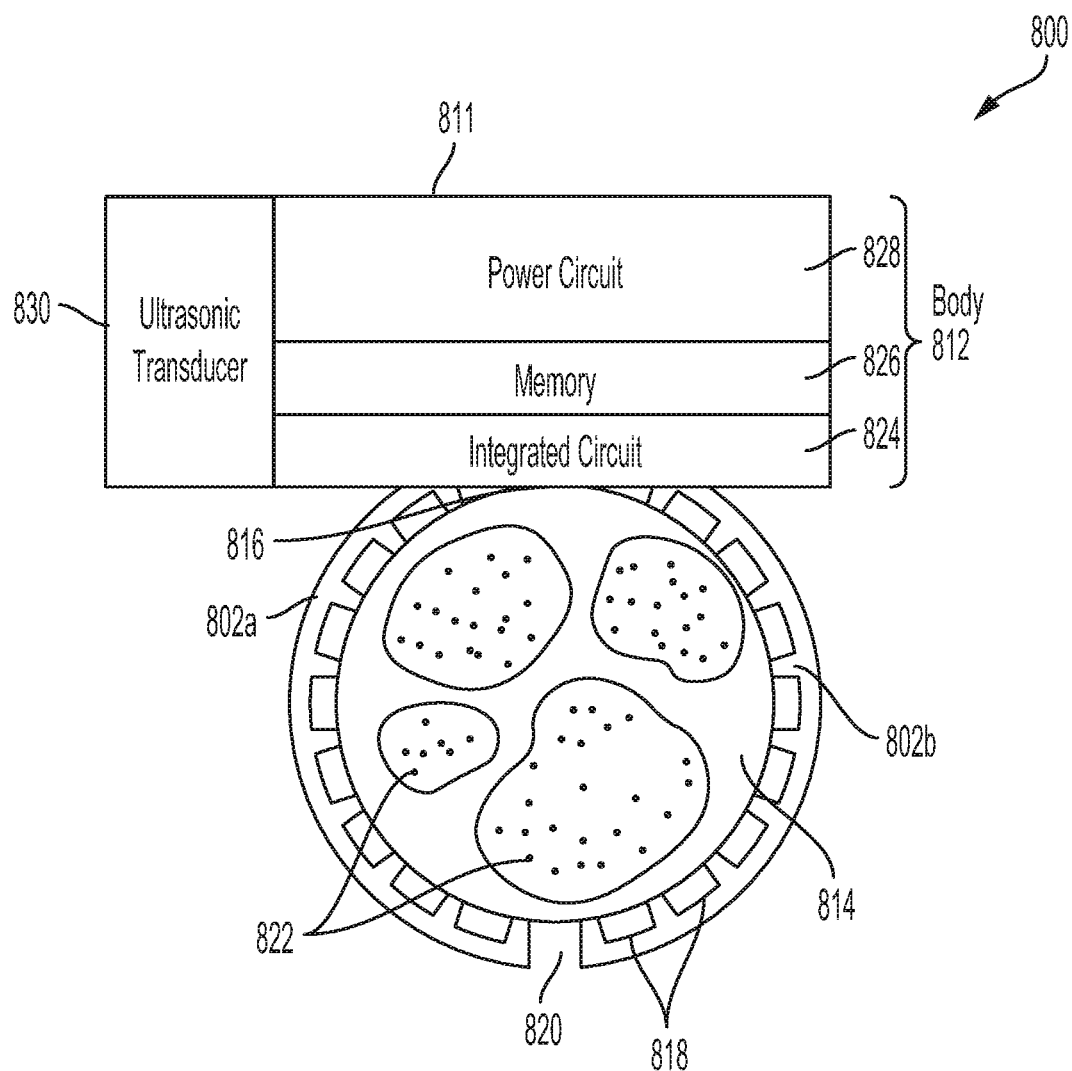
FIG. 8 illustrates a diagram of an implantable device configured to interact with a nerve of a subject, according to some embodiments.

FIG. 8 illustrates a diagram 800 of an implantable device 811 configured to interact with a nerve 814 of a subject, according to some embodiments. In some embodiments, implantable device 811 can be an example implementation of implantable device 104 as described above with respect to FIG. 1. As shown in diagram 800, implantable device 811 can be implanted on nerve 814 and include one or more curved member such as curved member 802 extending from a body 812. Body 812 of implantable device 811 can include integrated circuit 824 (including, e.g., modulation and demodulation circuit 112, stimulation circuit 114, detection circuit 116, or controller circuit 120), a non-transitory memory 826 (e.g., memory 180), a power circuit 828 (e.g., power circuit 130), and an ultrasonic transducer 830 (e.g., ultrasonic transducer 108 or ultrasonic transducer circuit 106). In some embodiments, body 812 includes a plurality of ultrasonic transducers including ultrasonic transducer 830. Accordingly, it is to be understood that ultrasonic transducer 830, as shown in diagram 800, may represent a plurality of ultrasonic transducers.

In some embodiments, ultrasonic transducer 830 can be configured to receive ultrasonic waves transmitted by an interrogator (e.g., interrogator 102 of FIG. 1 or interrogator 202 of FIG. 2) and convert the mechanical energy of the ultrasonic waves into an electrical signal having an electrical energy. In some embodiments, the ultrasonic waves can include one or more operating mode commands that are detected by integrated circuit 824 to set an operating mode of implantable device 811 to one operating mode from a plurality of operating modes. In some embodiments, the electrical signal includes electrical representations of the one or more operating mode commands.

In some embodiments, a portion of the electrical signal can be processed by power circuit 828 to power the components of implantable device 811. In some embodiments, power circuit 828 can include a power conveyor circuit (e.g., power conveyor circuit 134) configured to convert the electrical signal having a first voltage to a second signal having a second voltage to power various components of integrated circuit 824. In some embodiments, power circuit 828 can include a rectifying circuit (e.g., an active rectifier) to convert the electrical signal in an AC form to a DC form where the converted electrical signal may be associated with the first voltage. In some embodiments, the power conveyor circuit can include a charge pump to generate the second voltage greater than the first voltage. In some embodiments, power circuit 828 can include an energy storage device (e.g., energy storage device 136) configured to store excess energy provided by the electrical signal and to operate as a secondary power source if the power supplied by the interrogator is insufficient. In some embodiments, the power conveyor circuit can be configured to control whether power is to be conveyed to or from the energy storage device, which effectively charges or discharges the energy storage device, respectively. In some embodiments, the power conveyor circuit can be configured control an amount of time (e.g., a number of clock cycles) that the power is conveyed in addition to the direction of power flow (e.g., in forward flow or in reverse flow).

In some embodiments, integrated circuit 824 includes a controller circuit (e.g., controller circuit 120) configured to set the operating mode of implantable device 811 based on an operating mode command received in the ultrasonic waves, as described above with respect to FIG. 1.

In some embodiments, the operating mode command can instruct implantable device 811 to enter a power calibration mode in which the controller circuit can generate information indicating whether more power or less power should be transmitted to the interrogator. In some embodiments, the controller circuit can be configured to generate this power information based on the available power as supplied by power circuit 828 and a power consumed by integrated circuit 824. In some embodiments, the available power includes the supply power provided by ultrasonic transducer 830 and accessible power provided by the energy storage device of power circuit 828. In some embodiments, the controller circuit can be configured to control ultrasonic transducer 830 to transmit to the interrogator the generated power information to cause the interrogator to control the wave power of transmitted ultrasonic waves. In some embodiments, the consumed power can be determined by the controller circuit based on an operating mode of implantable device 811, as described above with respect to FIG. 1.

In some embodiments, the operating mode command can instruct implantable device 811 to enter a nerve-stimulation mode or a detection mode, each of which may operate electrode pads 818 on curved member 802. In some embodiments, the detection mode may be an example of an uplink mode associated with transmitting device data to other devices such as an interrogator, as described above with respect to FIGS. 6B-7.

In some embodiments, in the detection mode, electrode pads 818 are configured to detect an electrophysiological signal, and a detection signal based on the electrophysiological signal is received by integrated circuit 824. The detection signal received by integrated circuit 824 may be processed (for example, amplified, digitized, and/or filtered) by a detection circuit (e.g., by detection circuit 116) before being received by the controller circuit. In some embodiments, the controller circuit can access non-transitory memory (e.g., memory 180) to store data related to the detected electrophysiological signal. In some embodiments, in the detection mode, the controller circuit can be configured to operate ultrasonic transducer 830 to emit a backscatter of received ultrasonic waves in which the backscattered ultrasonic waves encodes the data related to the detected electrophysiological signal.

In some embodiments, the operating mode command can instruct implantable device 811 to enter the nerve-stimulating mode. In the stimulation mode, the controller circuit can generate a stimulation signal based on the detection signal, and operate one or more electrode pads 818 to emit an electrical pulse to nerve 814 based on the stimulation signal. In some embodiments, the controller circuit can access the non-transitory memory (e.g., memory 180) to store data related to the stimulation signal or electrical pulse emitted to nerve 814. In some embodiments, in the stimulation mode, the controller circuit can be configured to operate ultrasonic transducer 830 to emit a backscatter of received ultrasonic waves in which the backscattered ultrasonic waves encodes data related a status of the stimulation.

Data stored on the non-transitory memory can be wirelessly transmitted through ultrasonic backscatter waves emitted by ultrasonic transducer 830. As described above with respect to FIG. 1, to transmit data using the ultrasonic backscatter, ultrasonic transducer 830 may first receive ultrasonic waves and generates an electrical current that flows through a modulation circuit. Then, the controller circuit may access the memory and operate the modulation circuit to modulate the electrical current flowing through the modulation circuit to encode the data. Through such a process, the ultrasonic backscatter waves emitted by ultrasonic transducer 830 can encode the data.

In some embodiments, as shown in diagram 800, curved member 802 can include a first portion 802a and a second portion 802b bridged by body 812 at point 816. In some embodiments, first portion 802a and second portion 802b are directly connected, and curved member 802 is attached to body 812 through a connecting member. Curved member 802 can include a plurality of electrode pads 818 on the inner surface of curved member 802, and electrode pads 818 can be radially positioned around an axis parallel to the length of nerve 814. A separation 820 between first portion 202a and second portion 202b is present along curved member 802 (which may be similarly present in other curved members of implantable device 811). In some embodiments, implantable device 811 can be implanted by flexing first portion 802a and second portion 802b of curved member 802 outwardly, thereby expanding the size of the separation and allowing nerve 814 or other filamentous tissue to pass through separation 820 and fit within the cylindrical space formed by curved member 802. First portion 802a and second portion 802b of curved member 802 can be released, which allows curved member 802 to wrap around nerve 814 or other filamentous tissue.

The plurality of electrode pads 818 of as shown in FIG. 8 are outside of nerve 814, but in direct contact with the epineurium of nerve 814. Nerve 814 can include several fascicles 822. In some embodiments, electrode pads 818 within curved member 802 can be operated for targeted emission of an electrical pulse to one or more of fascicles 822 or other subset of nerve fibers, and/or operated for targeted detection of an electrophysiological signal transmitted by one or more of fascicles 822 or other subset of nerve fibers. For example, electrode pads 818 can be selectively activated by the controller circuit within integrated circuit 824, which is housed within body 812, to emit an electric pulse targeted to one or more fascicles 822. In another example, electrode pads 818 are operated by the controller circuit to detect an electrophysiological signal transmitted by one or more of fascicles 822 within nerve 814. In some embodiment, curved member 802 can be configured to detect the electrophysiological signal transmitted by nerve 814 or a subset of nerve fibers, emit an electrical pulse to nerve 814 or targeted to a subset of nerve fibers, or both detect the electrophysiological signal transmitted by nerve 814 or a subset of nerve fibers and emit an electrical pulse to nerve 814 or targeted to a subset of nerve fibers. For example, implantable device 811 may include a plurality of curved members (including curved member 802) in which a first curved member can be configured to detect the electrophysiological signal transmitted by nerve 814 or a subset of nerve fibers, and a second curved member can be configured to emit an electrical pulse to nerve 814 or targeted to a subset of nerve fibers.

In some embodiments, curved member 802 can be sized to engage a selected nerve 814 or fibrous tissue containing nerve 814. Nerve 814 can be the spinal cord or a peripheral nerve. In some embodiments, nerve 814 is an autonomic nerve or a somatic nerve. In some embodiments, nerve 814 is a sympathetic nerve or a parasympathetic nerve. In some embodiments, nerve 814 is a vagus nerve, a mesenteric nerve, a splenic nerve, a sciatic nerve, a tibial nerve, a pudendal nerve, a celiac ganglion, a sacral nerve, or any branch thereof.

The size, shape, and spacing of curved member 802 on implantable device 811 can depend on the type and size of tissue that implantable device 811 engages. In some embodiments, two or more curved members of implantable device 811 are spaced by about 0.25 mm or more (such as about 0.5 mm or more, about 1 mm or more, about 2 mm or more, about 3 mm or more, about 4 mm or more, about 5 mm or more, about 6 mm or more, or about 7 mm or more). In some embodiments, the two or more curved members are space by about 8 mm or less (such as about 7 mm or less, about 6 mm or less, about 5 mm or less, about 4 mm or less, about 3 mm or less, about 2 mm or less, about 1 mm or less, or about 0.5 mm or less). By way of example, the two or more curved members can be spaced about 0.25 mm to about 0.5 mm, about 0.5 mm to about 1 mm, about 1 mm to about 2 mm, about 2 mm to about 3 mm, about 3 mm to about 4 mm, about 4 mm to about 5 mm, about 5 mm to about 6 mm, about 5 mm to about 7 mm, or about 7 mm to about 8 mm apart. The width of curved member 802 can also vary depending on the application of implantable device 811 or the tissue engaged by implantable device 811. In some embodiments, the width of curved member 802 is about 100 μm or more (such as about 150 μm or more, about 250 μm or more, about 500 μm or more, about 1 mm or more, or about 1.5 mm or more). In some embodiments, the width of curved member 502 is about 2 mm or less (such as about 1.5 mm or less, about 1 mm or less, about 500 μm or less, about 250 μm or less, or about 150 μm or less. In some embodiments, the width of curved members 502 is about 100 μm to about 2 mm (such as about 100 μm to about 150 μm, about 150 μm to about 250 μm, about 250 μm to about 500 μm, about 500 μm to about 1 mm, about 1 mm to about 1.5 mm, or about 1.5 mm to about 2 mm). The inner surface of curved member 802 form a cylindrical space through which nerve 814 and/or filamentous tissue passes. The diameter of the cylindrical space formed by curved member 802 depends on the target nerve and/or filamentous tissue that implantable device 811 will engage. In some embodiments, curved member 802 forms a cylindrical space with a diameter of about 50 μm to about 15 mm (for example, about 50 μm to about 100 μm, about 100 μm to about 250 μm, about 250 μm to about 500 μm, about 500 μm to about 1 mm, about 1 mm to about 1.5 mm, about 1.5 mm to about 2.5 mm, about 2.5 mm to about 5 mm, about 5 mm to about 10 mm, or about 10 mm to about 15 mm).

In some embodiments, implantable device 811 includes one or more additional securing members configured to secure implantable device 811 to the filamentous tissue. Such securing members can include, for example, loops for suturing the implantable device to anatomical structure (such as the filamentous tissue or nerve, or other tissue surrounding the filamentous tissue or nerve), pins, or clamps. For example, implantable device 811 can be sutured to the filamentous tissue or nerve 814, or tissue surrounding the filamentous tissue or nerve, to limit movement of implantable device 811 once implanted.

In some embodiment, curved member 802 of implantable device 811 can include a metal, metal alloy, ceramic, silicon, or a non-polymeric material. Curved member 802 may be flexible, and is preferably sprung such that curved member 802 can be positioned around nerve 814 and/or filamentous tissue. In some embodiments, curved member 802 or a portion of curved member 802 is coated with an elastomeric coating or a non-elastomeric coating, which is preferably bioinert, such as polydimethylsioloxane (PDMS), a silicone, a urethane polymer, a poly(p-xylylene)polymer (such as a poly(p-xylylene) polymer sold under the tradename PARYLENE®), or a polyimide. Curved member 802 can include a plurality of electrode pads 818 on an inner surface. In some embodiments, electrode pads 818 on the inner surface of curved member 802 are not coated with the elastomeric coating or the non-elastomeric polymer coating, although the inner surface may be coated with a conductive material (e.g., electroplated with a PEDOT polymer or a metal to improve electrical characteristics of the electrode pad). Accordingly, in some embodiments, only the outer surface of curved member 802 is coated with the coating. Optionally, the coating further coats the housing of body 812.

In some embodiments, the plurality of electrode pads 818 can include 3, 4, 5, 6, 7, 8, 9, 10, 11, 12, 13, 14, 15, 16, 17, 18, 19, 20, or more electrode pads, such as between about 3 and about 50 electrode pads, between about 3 and about 5 electrode pads, between about 5 and about 10 electrode pads, between about 10 and about 25 electrode pads, or between about 25 and about 50 electrode pads. In some embodiments, the electrode pads within the plurality of electrode pads 818 can be selectively activated by the controller circuit, which allows for targeted electrical pulse emission, as further described herein.

In some embodiments, electrode pads 818 can include any suitable conductive material, such as one or more of (or an alloy of one or more of) tungsten, platinum, palladium, gold, iridium, niobium, tantalum, or titanium. The material of the detecting electrode pads and the stimulating electrode pads may be the same or different. The size and shape of electrode pads 818 may also be the same or different. For example, electrode pads 818 on a given curved member 802 may be of the same or different size, and electrode pads on different curved members may be of the same or different size.

In some embodiments, electrode pads 818 of implantable device 811 are positioned by curved member 802 to be in electrical communication with nerve 814. In some embodiments, electrode pads 818 are not in direct contact with nerve 814 (for example outside and not indirect contact with nerve 814), but are in electrical communication with nerve 814. In some embodiments, electrode pads 818 are positioned within about 2 mm (e.g., within about 1.8 mm, within about 1.6 mm, within about 1.4 mm, within about 1.2 mm, within about 1.0 mm, within about 0.8 mm, within about 0.6 mm, within about 0.4 mm, or within about 0.2 mm) of nerve 814. In some embodiments, electrode pads 818 are configured to penetrate the epineurium of nerve 814 at one or more locations. For example, electrode pads 818 can be needle-shaped, which allows for penetration of the epineurium. In some embodiments, electrode pads 818 directly contact nerve 814, for example the epineurium of nerve 814.

In some embodiments, body 812 includes a housing, which can include a base, one or more sidewalls, and a top. The housing can enclose ultrasonic transducer 830 and integrated circuit 824. The housing may be sealed closed (for example by soldering or laser welding) to prevent interstitial fluid from coming in contact with ultrasonic transducer 830 or integrated circuit 824. The housing is preferably made from a bioinert material, such as a bioinert metal (e.g., steel or titanium) or a bioinert ceramic (e.g., titania or alumina). The housing (or the top of the housing) may be thin to allow ultrasonic waves to penetrate through the housing. In some embodiments, the thickness of the housing is about 100 micormeters (μm) or less in thickness, such as about 75 μm or less, about 50 μm or less, about 25 μm or less, or about 10 μm or less. In some embodiments, the thickness of the housing is about 5 μm to about 10 μm, about 10 μm to about 25 μm, about 25 μm to about 50 μm, about 50 μm to about 75 μm, or about 75 μm to about 100 μm in thickness.

In some embodiments, body 812 of implantable device 811 is relatively small, which allows for comfortable and long-term implantation while limiting tissue inflammation that is often associated with implantable medical devices. In some embodiments, the longest dimension of body 812 is about 10 mm or less, such as about 5 mm to about 9 mm, or about 6 mm to about 8 mm.

In some embodiments, body 812 includes a material, such as a polymer, within the housing. The material can fill empty space within the housing to reduce acoustic impedance mismatch between the tissue outside of the housing and within the housing. Accordingly, body 812 is preferably void of air or vacuum, according to some embodiments.

In some embodiments, ultrasonic transducer 830 can include a micro machined ultrasonic transducer, such as a capacitive micro-machined ultrasonic transducer (CMUT) or a piezoelectric micro-machined ultrasonic transducer (PMUT), or can include a bulk piezoelectric transducer. Bulk piezoelectric transducers can be any natural or synthetic material, such as a crystal, ceramic, or polymer. Example bulk piezoelectric transducer materials may include barium titanate ($BaTiO_3$), lead zirconate titanate (PZT), zinc oxide (ZO), aluminum nitride (AlN), quartz, berlinite ($AlPO_4$), topaz, langasite ($La_3Ga_5SiO_{14}$), gallium orthophosphate ($GaPO_4$), lithium niobate ($LiNbO_3$), lithium tantalite ($LiTaO_3$), potassium niobate ($KNbO_3$), sodium tungstate ($Na_2WO_3$), bismuth ferrite ($BiFeO_3$), polyvinylidene (di)fluoride (PVDF), and lead magnesium niobate-lead titanate (PMN-PT).

In some embodiments, the bulk piezoelectric transducer is approximately cubic (i.e., an aspect ratio of about 1:1:1 (length:width:height)). In some embodiments, the piezoelectric transducer is plate-like, with an aspect ratio of about 5:5:1 or greater in either the length or width aspect, such as about 7:5:1 or greater, or about 10:10:1 or greater. In some embodiments, the bulk piezoelectric transducer is long and narrow, with an aspect ratio of about 3:1:1 or greater, with the longest dimension being aligned to the direction of the ultrasonic backscatter waves (i.e., the polarization axis). In some embodiments, one dimension of the bulk piezoelectric transducer is equal to one half of the wavelength (k) corresponding to the drive frequency or resonant frequency of the transducer. At the resonant frequency, the ultrasound wave impinging on either the face of the transducer will undergo a 180° phase shift to reach the opposite phase, causing the largest displacement between the two faces. In some embodiments, the height of the piezoelectric transducer is about 10 µm to about 1000 µm (such as about 40 µm to about 400 µm, about 100 µm to about 250 µm, about 250 µm to about 500 µm, or about 500 µm to about 1000 µm). In some embodiments, the height of the piezoelectric transducer is about 5 mm or less (such as about 4 mm or less, about 3 mm or less, about 2 mm or less, about 1 mm or less, about 500 µm or less, about 400 µm or less, 250 µm or less, about 100 µm or less, or about 40 µm or less). In some embodiments, the height of the piezoelectric transducer is about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in length.

In some embodiments, ultrasonic transducer 830 has a length of about 5 mm or less (such as about 4 mm or less, about 3 mm or less, about 2 mm or less, about 1 mm or less, about 500 µm or less, about 400 µm or less, 250 µm or less, about 100 µm or less, or about 40 µm or less) in the longest dimension. In some embodiments, ultrasonic transducer 830 has a length of about 20 µm or more (such as about 40 µm or more, about 100 µm or more, about 250 µm or more, about 400 µm or more, about 500 µm or more, about 1 mm or more, about 2 mm or more, about 3 mm or more, or about 4 mm or more) in the longest dimension.

In some embodiments, ultrasonic transducer 830 is connected to two electrodes to allow electrical communication with integrated circuit 824. The first electrode is attached to a first face of ultrasonic transducer 830 and the second electrode is attached to a second face of ultrasonic transducer 830, with the first face and the second face on opposite sides of ultrasonic transducer 830 along one dimension. In some embodiments, the electrodes include silver, gold, platinum, platinum-black, poly(3,4-ethylenedioxythiophene (PEDOT)), a conductive polymer (such as conductive PDMS or polyimide), or nickel. In some embodiments, the axis between the electrodes of ultrasonic transducer 830 is orthogonal to the motion of ultrasonic transducer 830.

The foregoing description sets forth exemplary methods, parameters and the like. It should be recognized, however, that such description is not intended as a limitation on the scope of the present disclosure but is instead provided as a description of exemplary embodiments. The illustrative embodiments described above are not intended to be exhaustive or to limit the disclosure to the precise forms disclosed. Many modifications and variations are possible in view of the above teachings. The embodiments were chosen and described to best explain the principles of the disclosed techniques and their practical applications. Others skilled in the art are thereby enabled to best utilize the techniques and various embodiments with various modifications as are suited to the particular use contemplated.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims. In the foregoing description of the disclosure and embodiments, reference is made to the accompanying drawings, in which are shown, by way of illustration, specific embodiments that can be practiced. It is to be understood that other embodiments and examples can be practiced, and changes can be made without departing from the scope of the present disclosure.

Although the foregoing description uses terms first, second, etc. to describe various elements, these elements should not be limited by the terms. These terms are only used to distinguish one element from another.

Reference to "about" or "approximately" a value or parameter herein includes (and describes) variations that are directed to that value or parameter per se. For example, description referring to "about X" includes description of "X."

It is understood that aspects and variations of the invention described herein include "consisting" and/or "consisting essentially of" aspects and variations.

The terms "implantable" and "implanted" refer to an object being fully implantable or fully implanted in a subject such that no portion of the object breaches the surface of the subject.

The term "substantially" refers to 90% or more. For example, a curved member that substantially surrounds a cross-section of a nerve refers to a curved member that surrounds 90% or more of the cross-section of the nerve.

The term "subject" and "patient" are used interchangeably herein to refer to a vertebrate animal such as a human.

The terms "treat," "treating," and "treatment" are used synonymously herein to refer to any action providing a benefit to a subject afflicted with a disease state or condition, including improvement in the condition through lessening, inhibition, suppression, or elimination of at least one symptom, delay in progression of the disease or condition, delay in recurrence of the disease or condition, or inhibition of the disease or condition.

Where a range of values is provided, it is to be understood that each intervening value between the upper and lower limit of that range, and any other stated or intervening value in that stated range, is encompassed within the scope of the present disclosure. Where the stated range includes upper or lower limits, ranges excluding either of those included limits are also included in the present disclosure.

In addition, it is also to be understood that the singular forms "a," "an," and "the" used in the foregoing description are intended to include the plural forms as well, unless the context clearly indicates otherwise. It is also to be understood that the term "and/or" as used herein refers to and encompasses any and all possible combinations of one or more of the associated listed items. It is further to be understood that the terms "includes, "including," "comprises," and/or "comprising," when used herein, specify the presence of stated features, integers, steps, operations, elements, components, and/or units but do not preclude the presence or addition of one or more other features, integers, steps, operations, elements, components, units, and/or groups thereof.

The term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

Features and preferences described above in relation to "embodiments" are distinct preferences and are not limited only to that particular embodiment; they may be freely combined with features from other embodiments, where technically feasible, and may form preferred combinations of features. The description is presented to enable one of ordinary skill in the art to make and use the invention and is provided in the context of a patent application and its requirements. Various modifications to the described embodiments will be readily apparent to those persons skilled in the art and the generic principles herein may be applied to other embodiments. Thus, the present invention is not intended to be limited to the embodiment shown but is to be accorded the widest scope consistent with the principles and features described herein.

What is claimed is:

1. A method of operating an implantable device, comprising, at the implantable device:
   receiving ultrasonic waves comprising an operating mode command;
   determining that the operating mode command comprises a pattern from a plurality of predetermined patterns; and
   setting an operating mode of the implantable device to one operating mode from a plurality of operating modes based on the pattern, wherein the plurality of operating modes comprises a downlink mode for downloading data from the received ultrasonic waves and an uplink mode for uploading data generated at the implantable device.

2. The method of claim 1, wherein the ultrasonic waves are transmitted by an interrogator.

3. The method of claim 1, wherein the ultrasonic waves are transmitted by another implantable device.

4. The method of claim 1, wherein determining that the operating mode command comprises the pattern comprises determining that a first portion of the operating mode command corresponds to the determined pattern.

5. The method of claim 4, wherein the first portion comprises a single pulse that indicates a start of the operating mode command.

6. The method of claim 1, wherein the plurality of predetermined patterns comprises a plurality of corresponding pulse durations, a plurality of corresponding amplitudes, or a plurality of corresponding phase or frequency changes.

7. The method of claim 1, wherein determining that the operating mode command comprises the pattern comprises:
   converting the ultrasonic waves into an electrical signal comprising a representation of the operating mode command; and
   counting a number of instances that a first portion of the electrical signal crosses a predefined voltage level, wherein the number of instances corresponds to the determined pattern.

8. The method of claim 4, wherein the determined pattern is associated with uploading data, and wherein the operating mode command comprises a second portion different from the first portion, comprising:
   setting the operating mode to the uplink mode for uploading device data associated with the uplink mode; and
   backscattering the ultrasonic waves, wherein the backscattered ultrasonic waves encode the device data in a backscatter of the second portion of the operating mode command.

9. The method of claim 8, wherein:
   the uplink mode comprises an acknowledgement mode and the device data comprises an acknowledgement that the implantable device successfully extracted an operating instruction from second ultrasonic waves received by the implantable device;
   the uplink mode comprises a physiological-condition reporting mode, and wherein the device data comprises information associated with a physiological condition detected by the implantable device in the physiological-condition reporting mode; or
   the uplink mode comprises a neural-activity reporting mode, and wherein the device data comprises information associated with an electrophysiological signal detected by the implantable device in the neural-activity reporting mode.

10. The method of claim 8, wherein the device data comprises information associated with an electrical pulse emitted by the implantable device, and wherein the electrical pulse is configured to modulate activity of a target nerve.

11. The method of claim 10, wherein the implantable device is configured to emit the electrical pulse in response to an operating instruction extracted from second ultrasonic waves received by the implantable device when the operating mode of the implantable device was set to a downlink mode.

12. The method of claim 4, wherein the determined pattern is associated with downloading data, and wherein the operating mode command comprises a second portion different from the first portion, comprising:
    setting the operating mode to the downlink mode for extracting data from the second portion of the operating mode command.

13. The method of claim 12, wherein the extracted data is associated with measuring a physiological condition, and wherein the method comprises, in response to extracting the data, measuring the physiological condition.

14. The method of claim 13, wherein the physiological condition comprises a temperature, a pulse rate, a blood pressure, a pH level, a presence of an analyte, or a concentration of the analyte.

15. The method of claim 12, wherein:
    the extracted data is associated with recording an electrophysiological signal, wherein the implantable device comprises two or more electrodes that are in electrical communication with a nerve of a subject, and wherein the two or more electrodes are configured to record the electrophysiological signal; or
    the extracted data is associated with stimulating a nerve, wherein the implantable device comprises two or more electrodes that are in electrical communication with the nerve of a subject, and wherein the method comprises: emitting one or more electrical pulses configured to modulate activity of the nerve using the two or more electrodes in response to the data extracted from the second portion.

16. The method of claim 1, comprising:
    maintaining a current operating state of the implantable device based on operation logic that define transitions between operating states, wherein the implantable device is configured to operate according to the current operating state;
    transitioning from the current operating state to a next operating state of the operation logic based on the operating mode command; and
    configuring the implantable device to operate according to the next operating state.

17. The method of claim 1, wherein the uplink mode uses a backscatter of the received ultrasonic waves for uploading data generated at the implantable device.

18. An implantable device operated using ultrasonic waves, comprising:
    an ultrasonic transducer configured to receive ultrasonic waves comprising an operating mode command; and a controller circuit configured to:
determine that the operating mode command comprises a pattern from a plurality of predetermined patterns; and
set an operating mode of the implantable device to one operating mode from a plurality of operating modes based on the pattern, wherein the plurality of operating modes comprises a downlink mode for downloading data from the received ultrasonic waves and an uplink mode for uploading data generated at the implantable device.

19. The device of claim 18, wherein the ultrasonic transducer is configured to receive the ultrasonic waves from an interrogator.

20. The device of claim 18, wherein to determine that the operating mode command comprises the pattern, the controller circuit is configured to determine that a first portion of the operating mode command corresponds to the determined pattern.

21. The device of claim 20, wherein the first portion comprises a single pulse that indicates a start of the operating mode command.

22. The device of claim 18, wherein the plurality of predetermined patterns comprises a plurality of corresponding pulse durations, a plurality of corresponding amplitudes, or a plurality of corresponding phase or frequency changes.

23. The device of claim 18, wherein to determine that the operating mode command corresponds to the pattern:
the ultrasonic transducer is configured to convert the ultrasonic waves into an electrical signal comprising a representation of the operating mode command, and
the controller circuit is configured to count a number of instances that a first portion of the electrical signal crosses a predefined voltage level, wherein the number of instances corresponds to the determined pattern.

24. The device of claim 20, wherein the determined pattern is associated with uploading data, wherein the operating mode command comprises a second portion different from the first portion,
wherein the controller circuit is configured to set the operating mode to the uplink mode for uploading device data associated with the uplink mode; and
wherein the ultrasonic transducer is configured to backscatter the ultrasonic waves, wherein the backscattered ultrasonic waves encode the device data in a backscatter of the second portion of the operating mode command.

25. The device of claim 24, wherein:
the uplink mode comprises an acknowledgement mode and the device data comprises an acknowledgement that the implantable device successfully extracted an operating instruction from second ultrasonic waves received by the implantable device;
the uplink mode comprises a physiological-condition reporting mode, and wherein the device data comprises information associated with a physiological condition detected by the implantable device in the physiological-condition reporting mode; or
the uplink mode comprises a neural-activity reporting mode, and wherein the device data comprises information associated with an electrophysiological signal detected by the implantable device in the neural-activity reporting mode.

26. The device of claim 24, wherein the device data comprises information associated with an electrical pulse emitted by the implantable device, and wherein the electrical pulse is configured to modulate activity of a target nerve.

27. The device of claim 18, wherein the determined pattern is associated with downloading data, wherein the operating mode command comprises a second portion different from the first portion, and wherein the controller circuit is configured to set the operating mode to the downlink mode for extracting data from the second portion of the operating mode command.

28. The device of claim 27, wherein the extracted data is associated with measuring a physiological condition, and wherein the device comprises a detection circuit configured to measure the physiological condition in response to the data being extracted.

29. The device of claim 28, wherein the physiological condition comprises a temperature, a pulse rate, a blood pressure, a pH level, a presence of an analyte, or a concentration of the analyte.

30. The device of claim 27, wherein:
the extracted data is associated with recording an electrophysiological signal, wherein the device comprises two or more electrodes that are in electrical communication with a nerve of a subject, and wherein the two or more electrodes are configured to record the electrophysiological signal; or
the extracted data is associated with stimulating a nerve, wherein the device comprises two or more electrodes that are in electrical communication with the nerve of a subject, wherein the two or more electrodes are configured to emit one or more electrical pulses configured to modulate activity of the nerve in response to the data extracted from the second portion.

31. The device of claim 18, wherein the controller circuit is configured to:
maintain a current operating state of the implantable device based on operation logic that define transitions between operating states, wherein the implantable device is configured to operate according to the current operating state;
transition from the current operating state to a next operating state of the operation logic based on the operating mode command; and
configure the implantable device to operate according to the next operating state.

32. The device of claim 18, wherein, in the uplink mode, the controller is configured to use a backscatter of the received ultrasonic waves to upload data generated at the implantable device.

* * * * *